US012668816B2

(12) United States Patent
Nickells et al.

(10) Patent No.: US 12,668,816 B2
(45) Date of Patent: Jun. 30, 2026

(54) ANTI-APOPTOTIC VECTOR AND METHOD OF USING THE SAME

(71) Applicant: WISCONSIN ALUMNI RESEARCH FOUNDATION, Madison, WI (US)

(72) Inventors: Robert W. Nickells, Madison, WI (US); Gillian McLellan, Madison, WI (US); Ryan J. Donahue, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 532 days.

(21) Appl. No.: 18/250,158

(22) PCT Filed: Oct. 21, 2021

(86) PCT No.: PCT/US2021/056010
§ 371 (c)(1),
(2) Date: Apr. 21, 2023

(87) PCT Pub. No.: WO2022/087238
PCT Pub. Date: Apr. 28, 2022

(65) Prior Publication Data
US 2023/0392166 A1     Dec. 7, 2023

Related U.S. Application Data

(60) Provisional application No. 63/154,364, filed on Feb. 26, 2021, provisional application No. 63/094,704, filed on Oct. 21, 2020.

(51) Int. Cl.
| | |
|---|---|
| *C12N 15/86* | (2006.01) |
| *A61P 27/06* | (2006.01) |
| *C07K 14/47* | (2006.01) |

(52) U.S. Cl.
CPC .............. *C12N 15/86* (2013.01); *A61P 27/06* (2018.01); *C07K 14/4747* (2013.01); *C12N 2750/14143* (2013.01)

(58) Field of Classification Search
CPC ..................................................... C12N 15/86
See application file for complete search history.

(56) References Cited

U.S. PATENT DOCUMENTS

| | | | | |
|---|---|---|---|---|
| 7,253,269 B1 * | 8/2007 | Ohta | .................. | C07K 14/4702 536/23.1 |
| 7,396,664 B2 | 7/2008 | Daly et al. | | |
| 2003/0008837 A1 | 1/2003 | Kiefer et al. | | |

(Continued)

OTHER PUBLICATIONS

Pfeifer, (1990), Proc. Natl. Acad. Sci. 87 (21), 8252-8256 (Year: 1990).*

(Continued)

*Primary Examiner* — Mark L Shibuya
(74) *Attorney, Agent, or Firm* — Quarles & Brady LLP

(57) ABSTRACT

The present invention provides vectors for delivery of an anti-apoptotic therapy. The vectors include a phosphoglycerate kinase (Pgk) promoter operably connected to a polynucleotide encoding an anti-apoptotic BCL2 protein (e.g., $BCLX_L$). The vectors may be used in methods of treating conditions associated with apoptosis, including glaucoma.

20 Claims, 15 Drawing Sheets

Specification includes a Sequence Listing.

(56) References Cited

U.S. PATENT DOCUMENTS

| | | | |
|---|---|---|---|
| 2004/0043028 A1* | 3/2004 | Lee | C07K 14/4747 |
| | | | 435/325 |
| 2010/0292200 A1 | 11/2010 | Kile et al. | |
| 2014/0364336 A1 | 12/2014 | Aldred et al. | |
| 2016/0194660 A1 | 7/2016 | Ye | |
| 2017/0096683 A1 | 4/2017 | Scaria et al. | |
| 2021/0340523 A1* | 11/2021 | Yao | C07K 16/303 |
| 2021/0388343 A1* | 12/2021 | Lisowski | C12Q 1/6844 |
| 2022/0170044 A1* | 6/2022 | Cobbold | C07K 14/70578 |

OTHER PUBLICATIONS

GenBank M60581.1, Pri 26-Jul. 2016 (Year: 2016).*
McCarty (2008), Molecular Therapy, vol. 16, No. 10, 1648-1656. (Year: 2008).*
Alavian, K. N. et al. Bcl-x L regulates metabolic efficiency of neurons through interaction with the mitochondrial F1 FO ATP synthase. Nat. Cell Biol. 13, 1224-1233 (2011).
Anderson, D. R. & Hendrickson, A. Effect of Intraocular Pressure on Rapid Axoplasmic Transport in Monkey Optic Nerve. Investig. Ophthalmol. Vis. Sci. 13, 771-783 (1974).
Arbel, N., Ben-Hail, D. & Shoshan-Barmatz, V. Mediation of the antiapoptotic activity of Bcl-XL protein upon interaction with VDAC1 protein. J. Biol. Chem. 287, 23152-23161 (2012).
Benowitz, L. I. & Routtenberg, A. GAP-43: An intrinsic determinant of neuronal development and plasticity. Trends Neurosci. 20, 84-91 (1997).
Berman, S. B. et al. Bcl-x L increases mitochondrial fission, fusion, and biomass in neurons. J. Cell Biol. 184, 707-719 (2009).
Bosco, A. et al. Complement C3-Targeted Gene Therapy Restricts Onset and Progression of Neurodegeneration in Chronic Mouse Glaucoma. Mol. Ther. 26, 2379-2396 (2018).
Carrillo, G. L., Su, J., Monavarfeshani, A. & Fox, M. A. F-spondin is essential for maintaining circadian rhythms. Front. Neural Circuits 12, (2018).
Cereso et al., Proof of concept for AAV2/5-mediated gene therapy in iPSCderived retinal pigment epithelium of a choroideremia patient, Mol Ther Methods Clin Dev. 2014.
Chen, Y. bei et al. Bcl-x L regulates mitochondrial energetics by stabilizing the inner membrane potential. J. Cell Biol. 195, 263-276 (2011).
Donahue et al., "BclX gene therapy to prevent RGC degeneration after optic nerve crush and in the DBA/2J model of glaucoma", Poster presentation at the ISER/BFF Glaucoma Symposium 2019, Atlanta, GA, Oct. 24-26, 2019.
Donahue, R. J., Maes, M. E., Grosser, J. A. & Nickells, R. W. BAX-Depleted Retinal Ganglion Cells Survive and Become Quiescent Following Optic Nerve Damage. Mol. Neurobiol. 57, 1070-1084 (2020).
D'orsi, B., Mateyka, J. & Prehn, J. H. M. Control of mitochondrial physiology and cell death by the Bcl-2 family proteins Bax and Bok. Neurochemistry International 109, 162-170 (2017).
Duong et al., Comparative AAV-eGFP Transgene Expression Using Vector Serotypes 1-9, 7m8, and 8b in Human Pluripotent Stem Cells, RPEs, and Human and Rat Cortical Neurons, Stem Cells Int. 2019.
Edlich, , F. et al. Bcl-xL Retrotranslocates Bax from the Mitochondria into the Cytosol. Cell 145, 104-116 (2011).
Fernandes, K. A. et al. Role of SARM1 and DR6 in retinal ganglion cell axonal and somal degeneration following axonal injury. Exp. Eye Res. 171, 54-61 (2018).
Figley MD, Gu W, Nanson JD, Shi Y, Sasaki Y, Cunnea K, et al. SARM1 is a metabolic sensor activated by an increased NMN/NAD+ ratio to trigger axon degeneration. Neuron. 2021; 109:1118-36. doi: 10.1016/j.neuron.2021.02.009.
Goldner, R. & Yaron, A. TIR Axons Apart: Unpredicted NADase Controls Axonal Degeneration. Neuron 1239-1241 (2017). doi:10.1016/j.neuron.2017.03.005.

Gonzalez-Garcia, M. et al. bcl-x is expressed in embryonic and postnatal neural tissues and functions to prevent neuronal cell death. Proc. Natl. Acad. Sci. 92, 4304-4308 (1995).
Harder JM, Fernandes KA, Libby RT. The Bcl-2 family member BIM has multiple glaucoma-relevant functions in DBA/2J mice. Sci Rep. 2012;2:530. doi: 10.1038/srep00530.
Harder, J. M. et al. Anaphylatoxin Receptor C3AR1 Promotesoptic Nerve Degeneration in DBA/2J Mice. J. Neuroinflammation 17, (2020).
Harun-Or-Rashid, M. et al. MCT2 overexpression rescues metabolic vulnerability and protects retinal ganglion cells in two models of glaucoma. Neurobiol. Dis. 141, 104944 (2020).
Hendrickson, A., Yan, Y. H., Erickson, A., Possin, D. & Pow, D. Expression patterns of calretinin, calbindin and parvalbumin and their colocalization in neurons during development of Macaca monkey retina. Exp. Eye Res. 85, 587-601 (2007).
Howell, G. R. et al. Axons of retinal ganglion cells are insulted in the optic nerve early in DBA/2J glaucoma. J. Cell Biol. 179, 1523-1537 (2007).
Howell, G. R. et al. Molecular clustering identifies complement and endothelin induction as early events in a mouse model of glaucoma. J. Clin. Invest. 121, 1429-44 (2011).
International Search Report and Written Opinion for corresponding PCT Application No. PCT/US2021/056010, mailed Mar. 8, 2022, 12 pages.
John, S. W. M. et al. Essential iris atrophy, pigment dispersion, and glaucoma in DBA/2J mice. Investig. Ophthalmol. Vis. Sci. 39, 951-962 (1998).
Lawrence, P. M. & Studholme, K. M. Retinofugal projections in the mouse. J. Comp. Neurol. 522, 3733-3753 (2014).
Leske MC, Heijl A, Hussein M, Bengtsson B, Hyman L, Komaroff E, et al. Factors for glaucoma progression and the effect of treatment: the early manifest glaucoma trial. Arch Ophthalmol. 2003; 121:48-56. doi: 10.1001/archopht. 121.1.48.
Levin, L. A., Schlamp, C. L., Spieldoch, R. 366 L., Geszvain, K. M. & Nickells, R. W. Identification of the bcl-2 family of genes in the rat retina. Investig. Ophthalmol. Vis. Sci. 38, 2545-2553 (1997).
Li, C. et al. Bcl-XL affects Ca2+ homeostasis by altering expression of inositol 1,4,5-Trisphosphate receptors. Proc. Natl. Acad. Sci. 99, 9830-9835 (2002).
Li, Schlamp, C. L., Poulsen, K. P. & Nickells, R. W. Bax-dependent and Independent Pathways of Retinal Ganglion Cell Death Induced by Different Damaging Stimuli. Exp. Eye Res. 71, 209-213 (2000).
Li, Y., Schlamp, C. L. & Nickells, R. W. Experimental induction of retinal ganglion cell death in adult mice. Investig. Ophthalmol. Vis. Sci. 40, 1004-1008 (1999).
Libby, R. T. et al. Inherited glaucoma in DBA/2J mice: pertinent disease features for studying the neurodegeneration. Vis. Neurosci. 22, 637-648 (2005).
Libby, R. T. et al. Susceptibility to Neurodegeneration in a Glaucoma Is Modified by Bax Gene Dosage. PLoS Genet. 1, (2005).
Liu, X. H., Collier, R. J. & Youle, R. J. Inhibition of Axotomy-induced Neuronal Apoptosis by Extracellular Delivery of a Bcl-XL Fusion Protein. J. Biol. Chem. 276, 46326-46332 (2001).
Maes, M. E., Schlamp, C. L. & Nickells, R. W. Live-cell imaging to measure BAX recruitment kinetics to mitochondria during apoptosis. PLoS One 12, (2017).
Malik, J. M. I., Shevtsova, Z., Bähr, M. & Kügler, S. Long-term in vivo inhibition of CNS neurodegeneration by Bcl-XL gene transfer. Mol. Ther. 11, 373-381 (2005).
Martin, K. R. G. et al. Gene Therapy with Brain-Derived Neurotrophic Factor as a Protection: Retinal Ganglion Cells in a Rat Glaucoma Model. Investig. Opthalmology Vis. Sci. 44, 4357-4365 (2003).
Mosinger, Ogilvie, J., Deckwerth, T. L., Knudson, C. M. & Korsmeyer, S. J. Supression of developmental retinal cell death but not of photoreceptor degeneration in Bax-deficient mice. Invest. Ophthalmol. Vis. Sci. 39, 1713-1720 (1998).
Nickells, R. W. & Pelzel, H. R. Tools and resources for analyzing gene expression changes in glaucomatous neurodegeneration. Exp. Eye Res. 141, 99-110 (2015).
Nickells, R. W., Schmitt, H. M., Maes, M. E. & Schlamp, C. L. AAV2-Mediated Transduction of the Mouse Retina After Optic Nerve Injury. Investig. Opthalmology Vis. Sci. 58, 6091 (2017).

(56)     References Cited

OTHER PUBLICATIONS

Nikolaev, A., McLaughlin, T., O'Leary, D. D. M. & Tessier-Lavigne, M. APP binds DR6 to trigger axon pruning and neuron death via distinct caspases. Nature 457, 981-989 (2009).

Osterloh, J. M. et al. dSarm/Sarm1 is required for activation of an injury-induced axon death pathway. Science (80-.). 337, 481-484 (2012).

Parsadanian, A. S., Cheng, Y., Keller-Peck, C. R., Holtzman, D. M. & Snider, W. D. Bcl-x(L) is an antiapoptotic regulator for postnatal CNS neurons. J. Neurosci. 18, 1009-1019 (1998).

Pena JC, Rudin CM, Thompson CB. A Bcl-x(L) transgene promotes malignant conversion of chemically initiated skin papillomas. Cancer Res. 1998;58:2111-6.

Quigley HA, Glaucoma. Lancet 2011;377:1367-77. doi: 10.1016/S0140-6736(10)61423-7.

Ramirez-Komo JA, Delaney MA, Straign D, Lukin K, Tsang M, Iritani BM, et al. Spontaneous loss of B lineage transcription factors leads to pre-B leukemia in Ebf1+/−Bcl-xLTg mice. Oncogenesis. 2017;6:e355. doi: 10.1038/oncsis.2017.55.

Robbins et al., Viral Vectors for Gene Therapy, Pharmacol. Ther. vol. 80, No. 1, pp. 35-47, 1998.

Schlamp, C. L. et al. Evaluation of the percentage of ganglion cells in the ganglion cell layer of the rodent retina. Mol. Vis. 19, 1387-1396 (2013).

Schlamp, C. L., Li, Y., Dietz, J. A., Janssen, K. T. & Nickells, R. W. Progressive ganglion cell loss and optic nerve degeneration in DBA/2J mice is variable and asymmetric. BMC Neurosci. 7, 1-14 (2006).

Schmitt, H. M., Grosser, J. A., Schlamp, C. L. & Nickells, R. W. Targeting HDAC3 in the DBA/2J spontaneous mouse model of glaucoma. Exp. Eye Res. 200, 108244 (2020).

Semaan, S. J. & Nickells, R. W. The apoptotic response in HCT116 cancer cells becomes rapidly saturated with increasing expression of a GFP-BAX fusion protein. BMC Cancer 10, (2010).

Simon, D. J. et al. A Caspase Cascade Regulating Developmental Axon Degeneration. J. Neurosci. 32, 17540-17553 (2012).

Simon, D. J. et al. Axon Degeneration Gated by Retrograde Activation of Somatic Pro apoptotic Signaling. Cell 164, 1031-1045 (2016).

Smith, R. S., John, S. W. M., Nishina, P. M. & Sundberg, J. P. Systematic Evaluation of the Mouse Eye: Anatomy, Pathology, and Biomethods. (CRC Press, 2001).doi:https://doi.org/10.1201/9781420041606.

Stieger, K., Lhériteau, E., Moullier, P. & Rolling, F. AAV-mediated gene therapy for retinal disorders in large animal models. ILAR Journal 50, 206-224 (2009).

Summers, D. W., DiAntonio, A. & Milbrandt, J. Mitochondrial dysfunction induces Sarm1-dependent cell death in sensory neurons. J. Neurosci. 34, 9338-9350 (2014).

Sun, Y. F., Yu, L. Y., Saarma, M., Timmusk, T. & Arumae, U. Neuron-specific Bcl-2 homology 3 domain-only splice variant of Bak is anti-apoptotic in neurons, but pro apoptotic in non-neuronal cells. J. Biol. Chem. 276, 16240-16247 (2001).

Vervliet, T. et al. Ryanodine receptors are targeted by anti-apoptotic Bcl-XL involving its BH4 domain and Lys87 from its BH3 domain. Sci. Rep. 5, (2015).

Viar, K., Njoku, D., Secor McVoy, J. & Oh, U. Sarm1 knockout protects against early but not late axonal degeneration in experimental allergic encephalomyelitis. PLoS One 15, e0235110 (2020).

Wang, D., Tai, P. W. L. & Gao, G. Adeno-associated virus vector as a platform for gene therapy delivery. Nat. Rev. Drug Discov. 18, 358-378 (2019).

Weng, C. Y. Bilateral Subretinal Voretigene Neparvovec-rzyl (Luxturna) Gene Therapy. Ophthalmol. Retin. 3, 450 (2019).

Williams, P. A. et al. Vitamin B3 modulates mitochondrial vulnerability and prevents glaucoma in aged mice. Science (80-.). 355, 756-760 (2017).

Wyzewski Z, Świtlik W, Mielcarska MB, Gregorczyk-Zboroch KP. The role of Bcl-Xl protein in viral infections. Int J Mol Sci. 2021;22:1-16. doi: 10.3390/ijms22041956.

Yin, W. et al. TAT-mediated delivery of Bcl-xL protein is neuroprotective against neonatal hypoxic-ischemic brain injury via inhibition of caspases and AIF. Neurobiol. Dis. 21, 358-371 (2006).

Donahue et al. Bclx gene therapy prevents BAX activation and preserves retinal ganglion cell axons in the DBA/2J glaucoma model. ARVO Annual Meeting Abstract. Published in: Investigative Ophthalmology & Visual Science 61(7):659, 2020.

Maes ME, Schlamp CL, Nickells RW. BAX to basics: How the BCL2 gene family controls the death of retinal ganglion cells. Prog Retin Eye Res. Mar. 2017;57:1-25.

* cited by examiner

G

SEQUENCE LISTING

```
<160> NUMBER OF SEQ ID NOS: 20

<210> SEQ ID NO 1
<211> LENGTH: 500
<212> TYPE: DNA
<213> ORGANISM: Mus musculus
<220> FEATURE:
<221> NAME/KEY: misc_feature
<222> LOCATION: (1)..(500)
<223> OTHER INFORMATION: PGK-1 promoter

<400> SEQUENCE: 1
gggtagggga ggcgcttttc ccaaggcagt ctggagcatg cgctttagca gccccgctgg      60
gcacttggcg ctacacaagt ggcctctggc ctcgcacaca ttccacatcc accggtaggc     120
gccaaccggc tccgttcttt ggtggcccct tcgcgccacc ttctactcct cccctagtca     180
ggaagttccc ccccgccccg cagctcgcgt cgtgcaggac gtgacaaatg gaagtagcac     240
gtctcactag tctcgtgcag atggacagca ccgctgagca atggaagcgg gtaggccttt     300
ggggcagcgg ccaatagcag ctttgctcct tcgctttctg ggctcagagg ctgggaaggg     360
gtgggtccgg gggcgggctc aggggcgggc tcaggggcgg ggcgggcgcc cgaaggtcct     420
ccggaggccc ggcattctgc acgcttcaaa agcgcacgtc tgccgcgctg ttctcctctt     480
cctcatctcc gggcctttcg                                                 500

<210> SEQ ID NO 2
<211> LENGTH: 531
<212> TYPE: DNA
<213> ORGANISM: Homo sapiens
<220> FEATURE:
<221> NAME/KEY: misc_feature
<222> LOCATION: (1)..(531)
<223> OTHER INFORMATION: PGK-1 promoter

<400> SEQUENCE: 2
attccacggg gttggggttg cgccttttcc aaggcagccc tgggtttgcg cagggacgcg      60
gctgctctgg gcgtggttcc gggaaacgca gcggcgccga ccctgggtct cgcacattct     120
tcacgtccgt tcgcagcgtc acccggatct tcgccgctac ccttgtgggc ccccggcga     180
```

-continued

```
cgcttcctgc tccgcccta agtcgggaag gttccttgcg gttcgcggcg tgccggacgt      240
gacaaacgga agccgcacgt ctcactagta ccctcgcaga cggacagcgc caggagcaa      300 tggcagcgcg ccgaccgcga tgggctgtgg ccaatagcgg ctgctcagca gggcgcgccg      360
agagcagcgg ccgggaaggg gcggtgcggg aggcggggtg tggggcggta gtgtgggccc      420
tgttcctgcc cgcgcggtgt tccgcattct gcaagcctcc ggagcgcacg tcggcagtcg      480
gctccctcgt tgaccgaatc accgacctct ctccccagct gtatttccaa a              531
```

```
<210> SEQ ID NO 3
<211> LENGTH: 26
<212> TYPE: DNA
<213> ORGANISM: Artificial Sequence
<220> FEATURE:
<223> OTHER INFORMATION: Synthetic - Primer

<400> SEQUENCE: 3
aaatgtctca gagcaaccgg gagctg                                          26
```

```
<210> SEQ ID NO 4
<211> LENGTH: 28
<212> TYPE: DNA
<213> ORGANISM: Artificial Sequence
<220> FEATURE:
<223> OTHER INFORMATION: Synthetic - Primer

<400> SEQUENCE: 4
cagtgtctgg tcacttccga ctgaagag                                        28
```

```
<210> SEQ ID NO 5
<211> LENGTH: 24
<212> TYPE: DNA
<213> ORGANISM: Artificial Sequence
<220> FEATURE:
<223> OTHER INFORMATION: Synthetic - Primer

<400> SEQUENCE: 5
tggccggctc gagaaatgtc tcag                                            24
```

```
<210> SEQ ID NO 6
<211> LENGTH: 30
<212> TYPE: DNA
<213> ORGANISM: Artificial Sequence
<220> FEATURE:
<223> OTHER INFORMATION: Synthetic - Primer

<400> SEQUENCE: 6
gattcagtaa gctttcactt ccgactgaag                                      30
```

```
<210> SEQ ID NO 7
<211> LENGTH: 702
<212> TYPE: DNA
<213> ORGANISM: Mus musculus
<220> FEATURE:
<221> NAME/KEY: misc_feature
<222> LOCATION: (1)..(702)
<223> OTHER INFORMATION: Murine BCLX (BCL2L1)

<400> SEQUENCE: 7
atgtctcaga gcaaccggga gctggtggtc gactttctct cctacaagct ttcccagaaa      60
ggatacagct ggagtcagtt tagtgatgtc gaagagaata ggactgaggc cccagaagaa      120
actgaagcag agaggagac ccccagtgcc atcaatggca acccatcctg gcacctggcg      180
```

-continued

```
gatagcccgg ccgtgaatgg agccactggc cacagcagca gtttggatgc gcgggaggtg      240
attcccatgg cagcagtgaa gcaagcgctg agagaggcag gcgatgagtt tgaactgcgg      300
taccggagag cgttcagtga tctaacatcc cagcttcaca taaccccagg gaccgcgtat      360
cagagctttg agcaggtagt gaatgaactc tttcgggatg gagtaaactg gggtcgcatc      420 gtggccttt tctcctttgg cggggcactg tgcgtggaaa gcgtagacaa ggagatgcag       480
gtattggtga tcggattgc aagttggatg gccacctatc tgaatgacca cctagagcct       540
tggatccagg agaacggcgg ctgggacact tttgtggatc tctacgggaa caatgcagca      600
gccgagagcc ggaaaggcca ggagcgcttc aaccgctggt tcctgacggg catgactgtg      660
gctggtgtgg ttctgctggg ctcactcttc agtcggaagt ga                        702
```

```
<210> SEQ ID NO 8
<211> LENGTH: 233
<212> TYPE: PRT
<213> ORGANISM: Mus musculus
<220> FEATURE:
<221> NAME/KEY: MISC_FEATURE
<222> LOCATION: (1)..(233)
<223> OTHER INFORMATION: Murine BCLX (BCL2L1)

<400> SEQUENCE: 8

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Glu Thr Glu Ala Glu Arg Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
145                 150                 155                 160

Val Leu Val Ser Arg Ile Ala Ser Trp Met Ala Thr Tyr Leu Asn Asp
                165                 170                 175

His Leu Glu Pro Trp Ile Gln Glu Asn Gly Gly Trp Asp Thr Phe Val
            180                 185                 190

Asp Leu Tyr Gly Asn Asn Ala Ala Ala Glu Ser Arg Lys Gly Gln Glu
        195                 200                 205

Arg Phe Asn Arg Trp Phe Leu Thr Gly Met Thr Val Ala Gly Val Val
    210                 215                 220

Leu Leu Gly Ser Leu Phe Ser Arg Lys
225                 230
```

```
<210> SEQ ID NO 9
<211> LENGTH: 591
<212> TYPE: DNA
```

<213> ORGANISM: Felis catus
<220> FEATURE:
<221> NAME/KEY: misc_feature
<222> LOCATION: (1)..(591)
<223> OTHER INFORMATION: Feline BCLX (BCL2L1)

<400> SEQUENCE: 9

```
atggcaaagc aaccttcaga tgtaagttct gagtgtgaca gagaaggtgg acaattgcag        60
cctgctgaga ggcctcctca gctcaggcct ggggcccca cctctctaca gacagagcag       120
caaggtaatc ctgaaggcga aggggaccgc tgcccccaag gcagccctca gggcccgctg       180
gccccaccag ccagccccgg gccttttgct accagatccc cgttttcat ctttgtcaga       240 agatcctccc tgctgtctcg atcctccagt gggtatttct cttttgacac agacaggagc       300
ccggcaccca tgagttgtga caaatcaaca caaaccccaa gtcctccttg ccaggccttc       360
aaccattatc tcagtgcaat ggcttccatg aggcagcctc aggctgtacc cgcagatatg       420
cgcccggaga tatggattgc acaagagttg cggcgtatcg gagacgaatt taatgcatat       480
tacccaagga gggtcttttt gaataattac caagcagccg aagcccagcc ccaaatgatt       540
atcttacgac tgttacgtta catcgtccgc ctggtatggc gattgcagtg a               591
```

<210> SEQ ID NO 10
<211> LENGTH: 196
<212> TYPE: PRT
<213> ORGANISM: Felis catus
<220> FEATURE:
<221> NAME/KEY: MISC_FEATURE
<222> LOCATION: (1)..(196)
<223> OTHER INFORMATION: Feline BCLX (BCL2L1)

<400> SEQUENCE: 10

```
Met Ala Lys Gln Pro Ser Asp Val Ser Ser Glu Cys Asp Arg Glu Gly
1               5                   10                  15

Gly Gln Leu Gln Pro Ala Glu Arg Pro Pro Gln Leu Arg Pro Gly Ala
            20                  25                  30

Pro Thr Ser Leu Gln Thr Glu Gln Gln Gly Asn Pro Glu Gly Glu Gly
            35                  40                  45

Asp Arg Cys Pro Gln Gly Ser Pro Gln Gly Pro Leu Ala Pro Pro Ala
        50                  55                  60

Ser Pro Gly Pro Phe Ala Thr Arg Ser Pro Phe Phe Ile Phe Val Arg
65                  70                  75                  80

Arg Ser Ser Leu Leu Ser Arg Ser Ser Ser Gly Tyr Phe Ser Phe Asp
                85                  90                  95

Thr Asp Arg Ser Pro Ala Pro Met Ser Cys Asp Lys Ser Thr Gln Thr
                100                 105                 110

Pro Ser Pro Pro Cys Gln Ala Phe Asn His Tyr Leu Ser Ala Met Ala
            115                 120                 125

Ser Met Arg Gln Pro Gln Ala Val Pro Ala Asp Met Arg Pro Glu Ile
        130                 135                 140

Trp Ile Ala Gln Glu Leu Arg Arg Ile Gly Asp Glu Phe Asn Ala Tyr
145                 150                 155                 160

Tyr Pro Arg Arg Val Phe Leu Asn Asn Tyr Gln Ala Ala Glu Ala Gln
                165                 170                 175

Pro Gln Met Ile Ile Leu Arg Leu Leu Arg Tyr Ile Val Arg Leu Val
            180                 185                 190

Trp Arg Leu Gln
        195
```

<210> SEQ ID NO 11
<211> LENGTH: 702
<212> TYPE: DNA
<213> ORGANISM: Canis lupus
<220> FEATURE:
<221> NAME/KEY: misc_feature
<222> LOCATION: (1)..(702)
<223> OTHER INFORMATION: Canine BCLX (BCL2L1)

<400> SEQUENCE: 11

```
atgtctcaga gcaaccggga gctggtggtt gactttctct cctacaagct ttcccagaaa      60
ggatacagct ggagtcagtt tagtgatgtg gaagagaaca gaactgaggc cccagaaggg     120
actgaatcag agatggagac ccccagtgcc atcaatggca acccatcctg gcacttggca     180
gacagccctg cggtgaatgg agccactggc cacagcagca gcttggatgc ccgggaggtg     240
atccccatgg cagcggtgaa acaagcgctg agggaggctg gggatgagtt tgaactgagg     300
taccggcggg cattcagtga cctgacatcc cagcttcaca tcaccccagg gacagcatat     360
cagagctttg agcaggtagt gaatgaactc ttccggatgg gggtgaactg gggtcgcatt     420
gtggcctttt tctccttcgg tggggcactg tgcgtggaga gcgtagacaa ggagatgcag     480
gtattggtga gtcggatcgc agcttggatg gccacttacc tgaatgacca cctagagcct     540
tggatccagg agaacggcgg ctgggatact tttgtggaac tctacgggaa caatgcagca     600
gccgagagcc ggaagggcca ggagcgcttc aaccgctggt tcctgacagg catgactgtg     660
gctggtgtgg ttctgctggg ctcgctcttc agtcggaaat ga                      702
```

<210> SEQ ID NO 12
<211> LENGTH: 233
<212> TYPE: PRT
<213> ORGANISM: Canis lupus
<220> FEATURE:
<221> NAME/KEY: MISC_FEATURE
<222> LOCATION: (1)..(233)
<223> OTHER INFORMATION: Canine BCLX (BCL2L1)

<400> SEQUENCE: 12

```
Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
        130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
```

```
                165                 170                 175
His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
        195                 200                 205

Arg Phe Asn Arg Trp Phe Leu Thr Gly Met Thr Val Ala Gly Val Val
    210                 215                 220

Leu Leu Gly Ser Leu Phe Ser Arg Lys
225                 230
```

```
<210> SEQ ID NO 13
<211> LENGTH: 720
<212> TYPE: DNA
<213> ORGANISM: Canis lupus
<220> FEATURE:
<221> NAME/KEY: misc_feature
<222> LOCATION: (1)..(720)
<223> OTHER INFORMATION: Canine BCL2

<400> SEQUENCE: 13
atggcgcacg ctgggcgaac agggtacgat aaccgggaga tagtgatgaa gtacatccac      60
tacaagctgt cgcagagggg ctacgagtgg gacgcgggag aggcgggcgc cgcgcccccg     120
ggggccgccc ccgcgccggg catcttctcc tcgcagcccg gccgcgcccc cgcgcccgcc     180
aggacctcgc cgcccccgcc ccccgccgcc ccgctgccg ccgccgccgc cgccgccgac      240
gccgcgggcc ccgcgcccag ccccgtgcca cctgtggtcc acctgaccct gcgccaggcc     300
ggcgacgact tctcccgccg ctaccgccgc gacttcgccg agatgtccag ccagctgcac     360
ctgacgccct tcaccgcgag gggacgcttt gccacggtgg tggaggagct cttcagggat     420
ggggtgaact gggggaggat tgtggccttc tttgagttcg gtggggtcat gtgtgtggag     480
agcgtcaacc gggagatgtc gcccctggtg gacaacatcg ccctgtggat gactgagtac     540
ctgaaccggc atctgcacac ctggatccag gacaacggag ctgggatgc ctttgtggaa      600 ctgtacggcc ccaccatgca gcctctgttt gacttctcct ggctgtctct gaaggcgctg     660
ctcagtctgg ccctggtggg agcttgcatc accctgggtg cctatctggg ccataagtga     720
```

```
<210> SEQ ID NO 14
<211> LENGTH: 239
<212> TYPE: PRT
<213> ORGANISM: Canis lupus
<220> FEATURE:
<221> NAME/KEY: MISC_FEATURE
<222> LOCATION: (1)..(239)
<223> OTHER INFORMATION: Canine BCL2

<400> SEQUENCE: 14

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Glu Ala Gly Ala Ala Pro Pro Gly Ala Ala Pro Ala Pro Gly Ile
        35                  40                  45

Phe Ser Ser Gln Pro Gly Arg Ala Pro Ala Pro Ala Arg Thr Ser Pro
    50                  55                  60

Pro Pro Pro Ala Ala Pro Ala Ala Ala Ala Ala Ala Ala Asp
65                  70                  75                  80

Ala Ala Gly Pro Ala Pro Ser Pro Val Pro Pro Val Val His Leu Thr
                85                  90                  95
```

```
Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
            115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Thr Met Gln Pro
            195                 200                 205

Leu Phe Asp Phe Ser Trp Leu Ser Leu Lys Ala Leu Leu Ser Leu Ala
    210                 215                 220

Leu Val Gly Ala Cys Ile Thr Leu Gly Ala Tyr Leu Gly His Lys
225                 230                 235
```

```
<210> SEQ ID NO 15
<211> LENGTH: 702
<212> TYPE: DNA
<213> ORGANISM: Homo sapiens
<220> FEATURE:
<221> NAME/KEY: misc_feature
<222> LOCATION: (1)..(702)
<223> OTHER INFORMATION: Human BCLX (BCL2L1)

<400> SEQUENCE: 15
atgtctcaga gcaaccggga gctggtggtt gactttctct cctacaagct ttcccagaaa      60
ggatacagct ggagtcagtt tagtgatgtg aagagaaca ggactgaggc cccagaaggg     120
actgaatcgg agatggagac ccccagtgcc atcaatggca acccatcctg cacctggca     180 gacagccccg cggtgaatgg agccactggc cacagcagca gtttggatgc ccgggaggtg     240
atccccatgg cagcagtaaa gcaagcgctg agggaggcag cgacgagtt tgaactgcgg     300 taccggcggg cattcagtga cctgacatcc cagctccaca tcaccccagg gacagcatat     360
cagagctttg aacaggtagt gaatgaactc ttccggatg gggtaaactg gggtcgcatt     420 gtggccttt tctccttcgg cggggcactg tgcgtggaaa gcgtagacaa ggagatgcag     480
gtattggtga gtcggatcgc agcttggatg gccacttacc tgaatgacca cctagagcct     540
tggatccagg agaacggcgg ctgggatact tttgtggaac tctatgggaa caatgcagca     600
gccgagagcc gaaagggcca ggaacgcttc aaccgctggt tcctgacggg catgactgtg     660
gccggcgtgg ttctgctggg ctcactcttc agtcggaaat ga                      702
```

```
<210> SEQ ID NO 16
<211> LENGTH: 233
<212> TYPE: PRT
<213> ORGANISM: Homo sapiens
<220> FEATURE:
<221> NAME/KEY: MISC_FEATURE
<222> LOCATION: (1)..(233)
<223> OTHER INFORMATION: Human BCLX (BCL2L1)

<400> SEQUENCE: 16

Met Ser Gln Ser Asn Arg Glu Leu Val Val Asp Phe Leu Ser Tyr Lys
1               5                   10                  15
```

-continued

```
Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
            195                 200                 205

Arg Phe Asn Arg Trp Phe Leu Thr Gly Met Thr Val Ala Gly Val Val
    210                 215                 220

Leu Leu Gly Ser Leu Phe Ser Arg Lys
225                 230
```

```
<210> SEQ ID NO 17
<211> LENGTH: 720
<212> TYPE: DNA
<213> ORGANISM: Homo sapiens
<220> FEATURE:
<221> NAME/KEY: misc_feature
<222> LOCATION: (1)..(720)
<223> OTHER INFORMATION: Human BCL2

<400> SEQUENCE: 17
atggcgcacg ctgggagaac agggtacgat aaccgggaga tagtgatgaa gtacatccat      60
tataagctgt cgcagagggg ctacgagtgg gatgcgggag atgtgggcgc cgcgcccccg     120
ggggccgccc ccgcaccggg catcttctcc tcccagcccg ggcacacgcc ccatccagcc     180
gcatcccggg acccggtcgc caggacctcg ccgctgcaga ccccggctgc ccccggcgcc     240
gccgcggggc ctgcgctcag cccggtgcca cctgtggtcc acctgaccct ccgccaggcc     300
ggcgacgact ctcccgccg ctaccgccgc gacttcgccg agatgtccag ccagctgcac     360
ctgacgccct tcaccgcgcg gggacgcttt gccacggtgg tggaggagct cttcagggac     420
ggggtgaact ggggggagga tgtggccttc tttgagttcg gtggggtcat gtgtgtggag     480
agcgtcaacc gggagatgtc gcccctggtg acaacatcg ccctgtggat gactgagtac     540
ctgaaccggc acctgcacac ctggatccag gataacggag ctgggatgc ctttgtggaa     600 ctgtacggcc ccagcatgcg gcctctgtt gatttctcct ggctgtctct gaagactctg     660
ctcagtttgg ccctggtggg agcttgcatc accctgggtg cctatctggg ccacaagtga     720
```

```
<210> SEQ ID NO 18
<211> LENGTH: 239
<212> TYPE: PRT
<213> ORGANISM: Homo sapiens
<220> FEATURE:
<221> NAME/KEY: MISC_FEATURE
<222> LOCATION: (1)..(239)
<223> OTHER INFORMATION: Human BCL2

<400> SEQUENCE: 18

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
            115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
            195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235

<210> SEQ ID NO 19
<211> LENGTH: 582
<212> TYPE: DNA
<213> ORGANISM: Homo sapiens
<220> FEATURE:
<221> NAME/KEY: misc_feature
<222> LOCATION: (1)..(582)
<223> OTHER INFORMATION: Human BCLW (BCL2L2)

<400> SEQUENCE: 19
atggcgaccc cagcctcggc cccagacaca cgggctctgg tggcagactt tgtaggttat      60
aagctgaggc agaagggtta tgtctgtgga gctggccccg gggagggccc agcagctgac     120
ccgctgcacc aagccatgcg ggcagctgga gatgagttcg agaccgctt ccggcgcacc      180 ttctctgatc tggcggctca gctgcatgtg accccaggct cagcccaaca acgcttcacc     240
caggtctccg atgaactttt tcaaggggggc cccaactggg gccgccttgt agccttcttt     300
gtctttgggg ctgcactgtg tgctgagagt gtcaacaagg agatggaacc actggtggga     360
```

-continued

```
caagtgcagg agtggatggt ggcctacctg gagacgcagc tggctgactg gatccacagc      420
agtgggggct gggcggagtt cacagctcta tacggggacg gggccctgga ggaggcgcgg      480
cgtctgcggg aggggaactg ggcatcagtg aggacagtgc tgacgggggc cgtggcactg      540
ggggccctgg taactgtagg ggcctttttt gctagcaagt ga                        582
```

```
<210> SEQ ID NO 20
<211> LENGTH: 193
<212> TYPE: PRT
<213> ORGANISM: Homo sapiens
<220> FEATURE:
<221> NAME/KEY: MISC_FEATURE
<222> LOCATION: (1)..(193)
<223> OTHER INFORMATION: Human BCLW (BCL2L2)

<400> SEQUENCE: 20
```

```
Met Ala Thr Pro Ala Ser Ala Pro Asp Thr Arg Ala Leu Val Ala Asp
1               5                   10                  15

Phe Val Gly Tyr Lys Leu Arg Gln Lys Gly Tyr Val Cys Gly Ala Gly
            20                  25                  30

Pro Gly Glu Gly Pro Ala Ala Asp Pro Leu His Gln Ala Met Arg Ala
        35                  40                  45

Ala Gly Asp Glu Phe Glu Thr Arg Phe Arg Arg Thr Phe Ser Asp Leu
    50                  55                  60

Ala Ala Gln Leu His Val Thr Pro Gly Ser Ala Gln Gln Arg Phe Thr
65                  70                  75                  80

Gln Val Ser Asp Glu Leu Phe Gln Gly Gly Pro Asn Trp Gly Arg Leu
                85                  90                  95

Val Ala Phe Phe Val Phe Gly Ala Ala Leu Cys Ala Glu Ser Val Asn
            100                 105                 110

Lys Glu Met Glu Pro Leu Val Gly Gln Val Gln Glu Trp Met Val Ala
        115                 120                 125

Tyr Leu Glu Thr Gln Leu Ala Asp Trp Ile His Ser Ser Gly Gly Trp
    130                 135                 140

Ala Glu Phe Thr Ala Leu Tyr Gly Asp Gly Ala Leu Glu Glu Ala Arg
145                 150                 155                 160

Arg Leu Arg Glu Gly Asn Trp Ala Ser Val Arg Thr Val Leu Thr Gly
                165                 170                 175

Ala Val Ala Leu Gly Ala Leu Val Thr Val Gly Ala Phe Phe Ala Ser
            180                 185                 190

Lys
```

ANTI-APOPTOTIC VECTOR AND METHOD OF USING THE SAME

CROSS-REFERENCE TO RELATED APPLICATIONS

This application is a national stage filing under 35 U.S.C. § 371 of International Patent Application No. PCT/US2021/056010, filed on Oct. 21, 2021, which claims priority to U.S. Provisional Application No. 63/094,704, filed on Oct. 21, 2020, and U.S. Provisional Application No. 63/154,364, filed on Feb. 26, 2021, the contents of which are all incorporated by reference in their entireties.

STATEMENT REGARDING FEDERALLY SPONSORED RESEARCH

This invention was made with government support under grant number EY012223 and EY016665 awarded by the National Institutes of Health. The government has certain rights in this invention.

SEQUENCE LISTING

A Sequence Listing accompanies this application and is submitted as an ASCII text file of the sequence listing named "960296_04187_ST25.txt" which is 24,463 bytes in size and was created on Oct. 20, 2021. The sequence listing is electronically submitted via EFS-Web with the application and is incorporated herein by reference in its entirety.

BACKGROUND

In glaucoma, blindness is caused by degeneration of retinal ganglion cells (RGCs), neurons that project axons from the retina to the brain. The most prominent risk factor for glaucoma is elevated intraocular pressure (IOP) [1], and currently, lowering IOP is the only viable treatment for this disease. While this treatment is often able to slow the progression of neurodegeneration [2], there is wide-spread acknowledgement that a therapeutic that directly targets the RGCs and their axons would significantly augment IOP-lowering therapies.

SUMMARY

In a first aspect, the present invention provides vectors comprising a phosphoglycerate kinase (Pgk) promoter operably connected to a polynucleotide encoding an anti-apoptotic BCL2 protein. The Pgk promoter comprises SEQ ID NO:1 (i.e., the mouse Pgk-1 promoter), SEQ ID NO:2 (i.e., the human Pgk-1 promoter), or a sequence having 80% identity to SEQ ID NO:1 or SEQ ID NO:2.

In a second aspect, the present invention provides pharmaceutical compositions comprising a vector disclosed herein and a pharmaceutically acceptable carrier.

In a third aspect, the present invention provides methods of treating a subject having a condition associated with apoptosis of a cell. The methods comprise administering a therapeutically effective amount of any one of the vectors or pharmaceutical compositions disclosed herein to the subject.

D: Cell loss was determined by quantifying the difference in nuclear density in the RGC layer of retinal wholemounts between the experimental and contralateral eye (mean±standard deviation). In all, 6-10 mice were used per group. n.s.=not significant. *P<0.05. **P<0.01.

Figure 5:
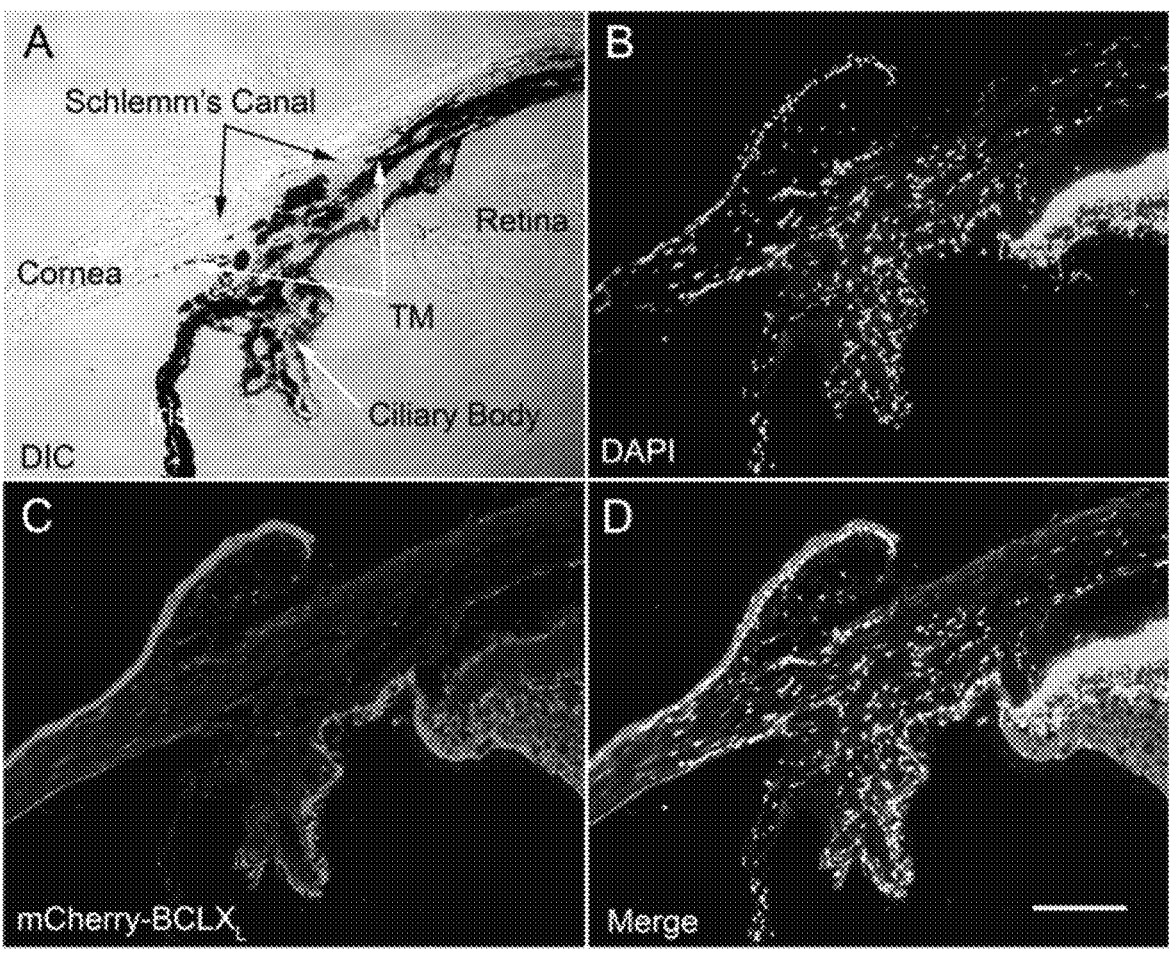
Figure 5:
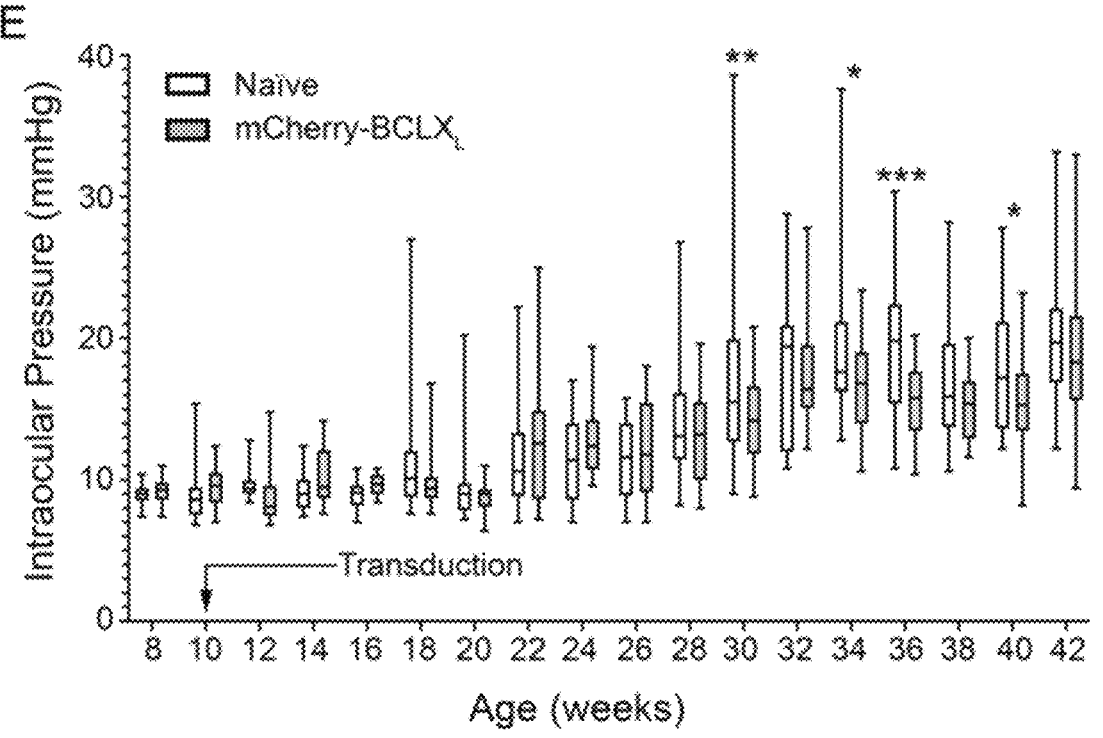

FIG. 5 demonstrates that AAV2-Pgk-mCherry-BclX$_L$ gene therapy does not alter the progression of ocular hypertension in DBA/2J mice. A: Brightfield image showing the relevant ocular anatomy for the outflow pathway of an eye that was transduced with AAV2-Pgk-mCherry-BclX$_L$. B-D: Fluorescent images showing the DAPI-positive nuclei (B) and the expression pattern of mCherry-BCLX$_L$ (C), as well as a combined view of B, C (D). Note that an mCherry antibody was used to amplify the mCherry-BCLX$_L$ signal. Expression is seen strongly in the retina and ciliary body but is not present in Schlemm's canal, the iris, or the trabecular meshwork (TM). The exterior surface of the cornea also appears to be expressing mCherry-BCLX$_L$, which may be the result of viral particles flowing onto the surface of the eye when the needle is removed from the eye during the intravitreal injection. E: Intraocular pressures of AAV2-Pgk-mCherry-BclX$_L$-transduced and naive DBA/2J mice that were measured every 2 weeks from the age of 8 to 42 weeks. Transduction occurred the day after the second measurement of IOP when the mice were 10 weeks old. The data are represented as box and whisker plots with the mean shown as a bar in the center of the data, the 25th and 75th percentiles shown as the edges of the box, and the whiskers extending to show the minimum and maximum values for the data. For IOP measurements, N=an average of 18 eyes per group per time point. Generalized Estimating Equation regression modeling was used to assess the statistical difference between the IOPs of the groups at each timepoint and longitudinally. Individual timepoints that are statistically different from one another are shown. *P<0.05, P<0.01, *P<0.001. Regression analysis performed on the data show that the longitudinal IOP progression of the naive and mCherry-BCLX$_L$ groups are similar.

Figure 6:
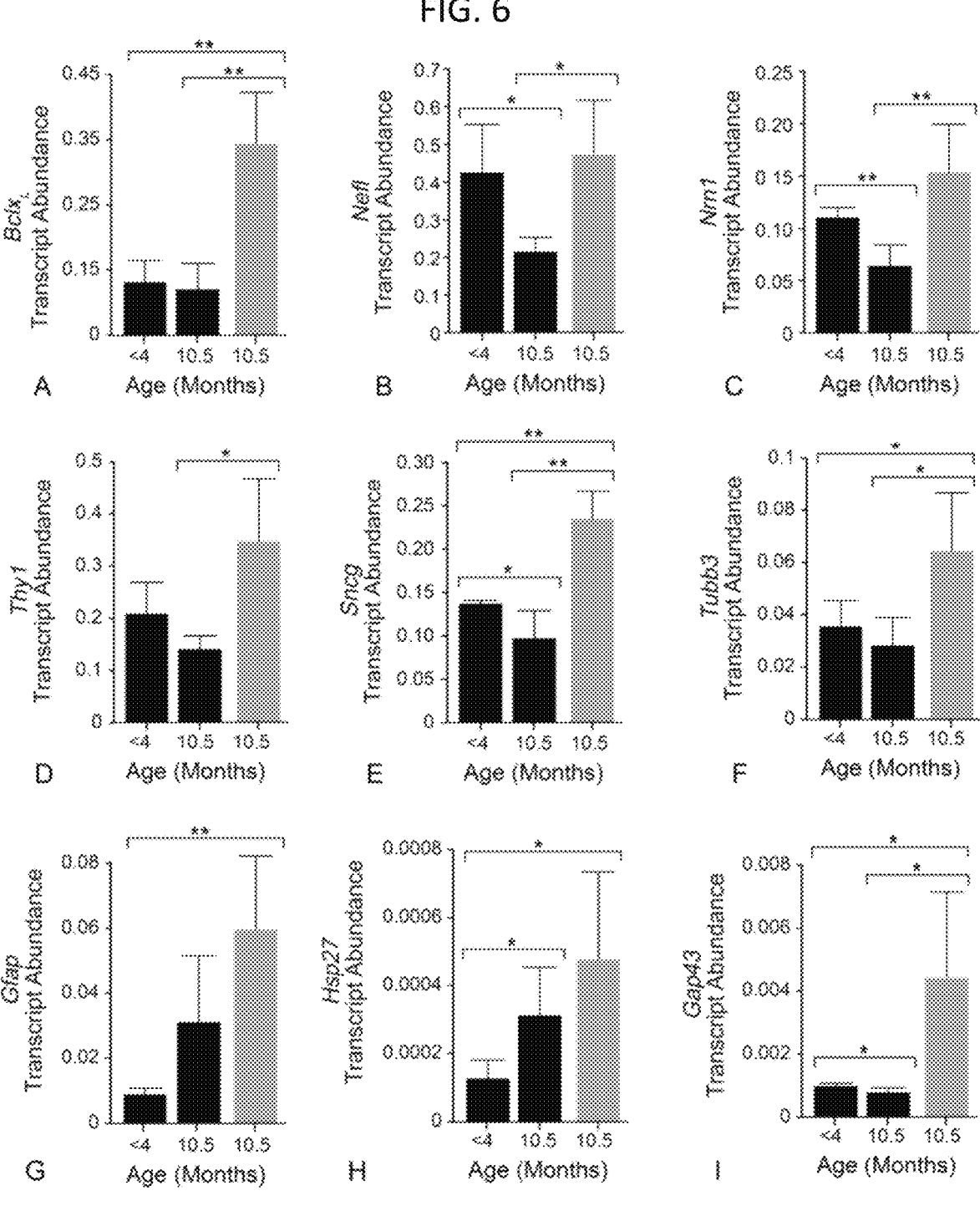

FIG. 6 demonstrates that BCLX$_L$ gene therapy attenuates RGC-specific transcript depletion in aged DBA/2J mice. Quantitative (real time) PCR was used to assess retinal gene expression in young mice and glaucomatous mice. A: BclX$_L$, expression was five times higher in transduced, aged DBA/2J mice (grey bars) than either young or 10.5-month-old naive animals (black bars). B-F: The transcript abundances of five RGC-specific/selective transcripts. RGC transcripts were consistently more abundant in aged mice that were BCLX$_L$ treated than age-matched mice that did not receive BCLX$_L$. G, H: The transcript abundance of Gfap and Hsp27, two transcripts produced in retinas experiencing glaucomatous stress. These transcripts were significantly more abundant in aged mice relative to the young mice that had not developed glaucoma. I: The transcript abundance of Gap43, a gene that has been associated with neuroregeneration. Gap43 was more abundant in BCLX$_L$-treated, 10.5-month-old mice than young or 10.5-month-old naive mice. Four groups of three pooled eyes were used for each experimental cohort. The graphs display the average abundance of the four groups and the error bars show the standard deviation from that average. All transcript levels are quantified as the number of target molecules present per molecule of S16 ribosomal protein mRNA. Statistical evaluation was made using unpaired t tests of the means (*P<0.05, **P<0.01).

Figure 7:
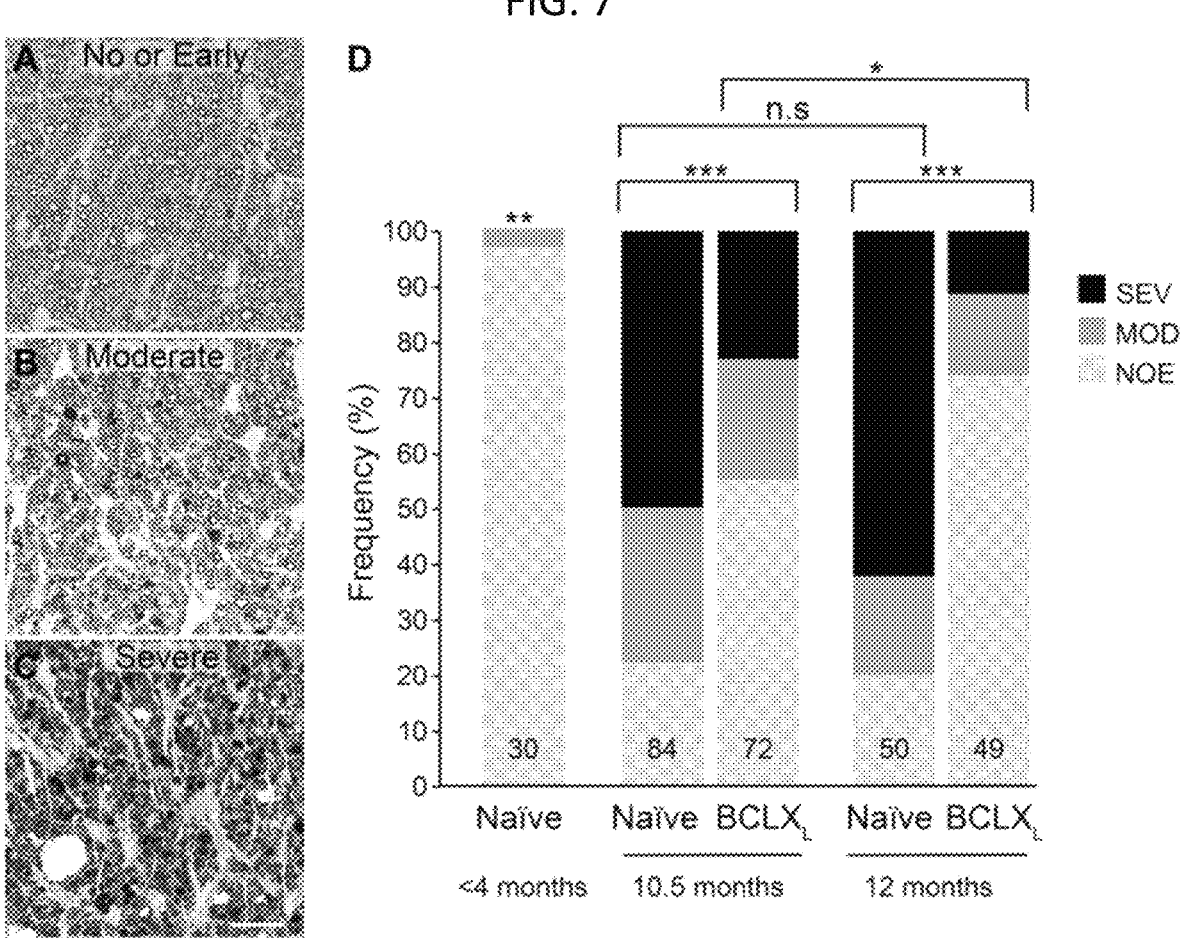

FIG. 7 demonstrates that mCherry-BCLX$_L$ gene therapy prevents optic nerve degeneration in aged DBA/2J mice. A-C: Examples of each potential optic nerve score. A: The no or early (NOE) glaucoma example has uniform distribution of axons and the glial cells occupy minimal space on the image. B: The moderate glaucoma (MOD) example has a large number of healthy axons but also displays increased dark spots (denoted by white arrows) where the myelin sheaths have collapsed around the axons. The glial cells may have become slightly enlarged but do not occupy much more space than the NOE example. C: The severe glaucoma (SEV) example has very few healthy axons, most of what remains are dark spots. The glial cells in this image have expanded and occupy a larger percentage of the image than either the NOE or moderate glaucoma examples. Scale bar=25 µm. D: Distributions of each of the three scores for each experimental group. The inset number denotes the number of optic nerves scored for each group. The distribution of mice for each cohort (M/F) was: <4 (4/12); 10.5 Naive (21/21); 10.5 BCLX$_L$ (22/15); 12 Naive (13/12); 12 BCLX$_L$ (11/14). $\chi^2$ tests were performed to assess the statistical differences between the distributions of scores of different groups. *P<0.01, P<0.00003 (young mice relative to all other cohorts in individual tests), *P<0.00001.

Figure 8:
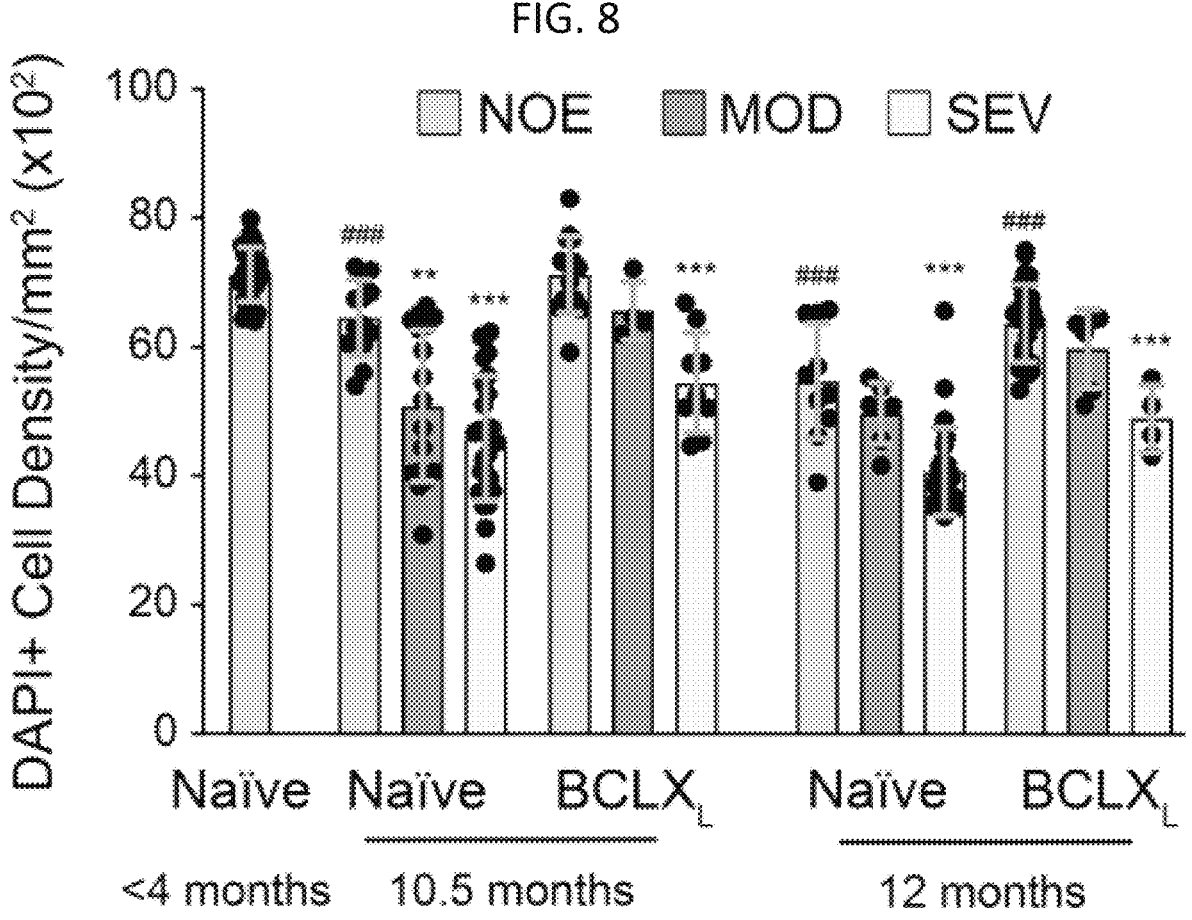

FIG. 8 shows the correlation between retinal total cell density and optic nerve degeneration score. Eyes for which there was both an optic nerve score and analysis of the total neuronal cell density present in the retina were used to evaluate the symmetry of both RGC soma loss and axon loss in the same eye. Total cell counts reflect both RGC and amacrine neuronal populations in the ganglion cell layer. Combined scatter plot/bar graphs (mean±standard deviation) are shown. In all cohorts (naive and BCLX$_L$ treated, aged 10.5 or 12 months), cell density was significantly lower in eyes with SEV optic nerves compared to eyes with NOE optic nerves in the same cohort (Student's t test, *P<0.0001). Also, within cohorts, eyes exhibiting MOD optic nerves had no significant change in cell density, compared to eyes with NOE optic nerves, with the exception of naive mice aged to 10.5 months (P=0.0006). Compared to young naive mouse eyes with NOE optic nerves, most aged cohorts had modestly reduced cell densities in the NOE populations (on average a 10% reduction, [###]P<0.001), with the exception of BCLX$_L$-treated eyes at 10.5 months, which showed no significant change. The distribution of mice for each cohort (M/F) was: <4 (6/10); 10.5 Naive (17/12); 10.5 BCLX$_L$ (10/5); 12 Naive (12/11); 12 BCLX$_L$ (8/12).

Figure 9:
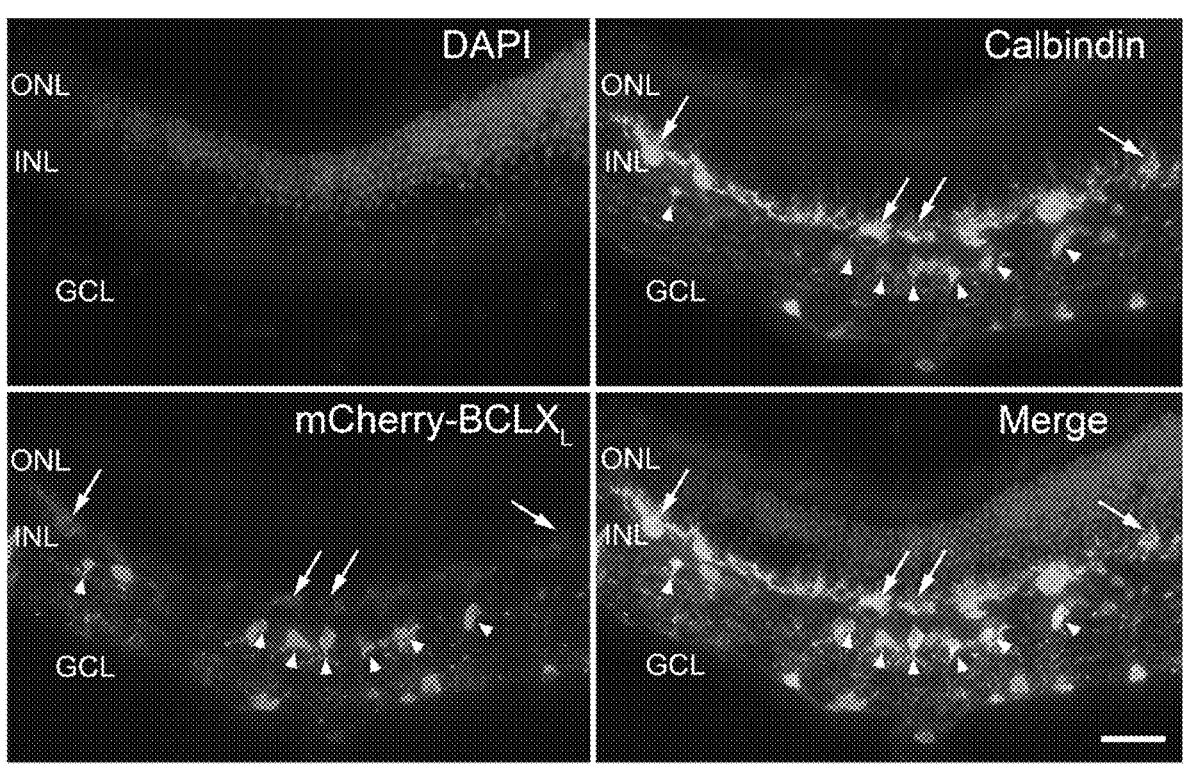

FIG. 9 shows images of a retinal section showing co-localization of the mCherry-BCLX$_L$ transgene and calbindin. Intravitreal injection of AAV2-Pgk-mCherry-BclX$_L$, results in modest transduction of cells in both the inner nuclear layer (INL) and ganglion cell layer (GCL). Counter staining with an antibody to calbindin indicates that these cells are likely horizontal neurons (arrows) that exhibit weak expression of the transgene, and a population of amacrine cells (arrowheads) that exhibit strong transgene expression. Cells in the GCL that are transduced and co-localize with calbindin could be either amacrine cells or retinal ganglion cells[55]. No transgene expressing cells in the outer nuclear layer (ONL) were detected. Individual channels are shown. Scale bar=70 µm.

Figure 10:
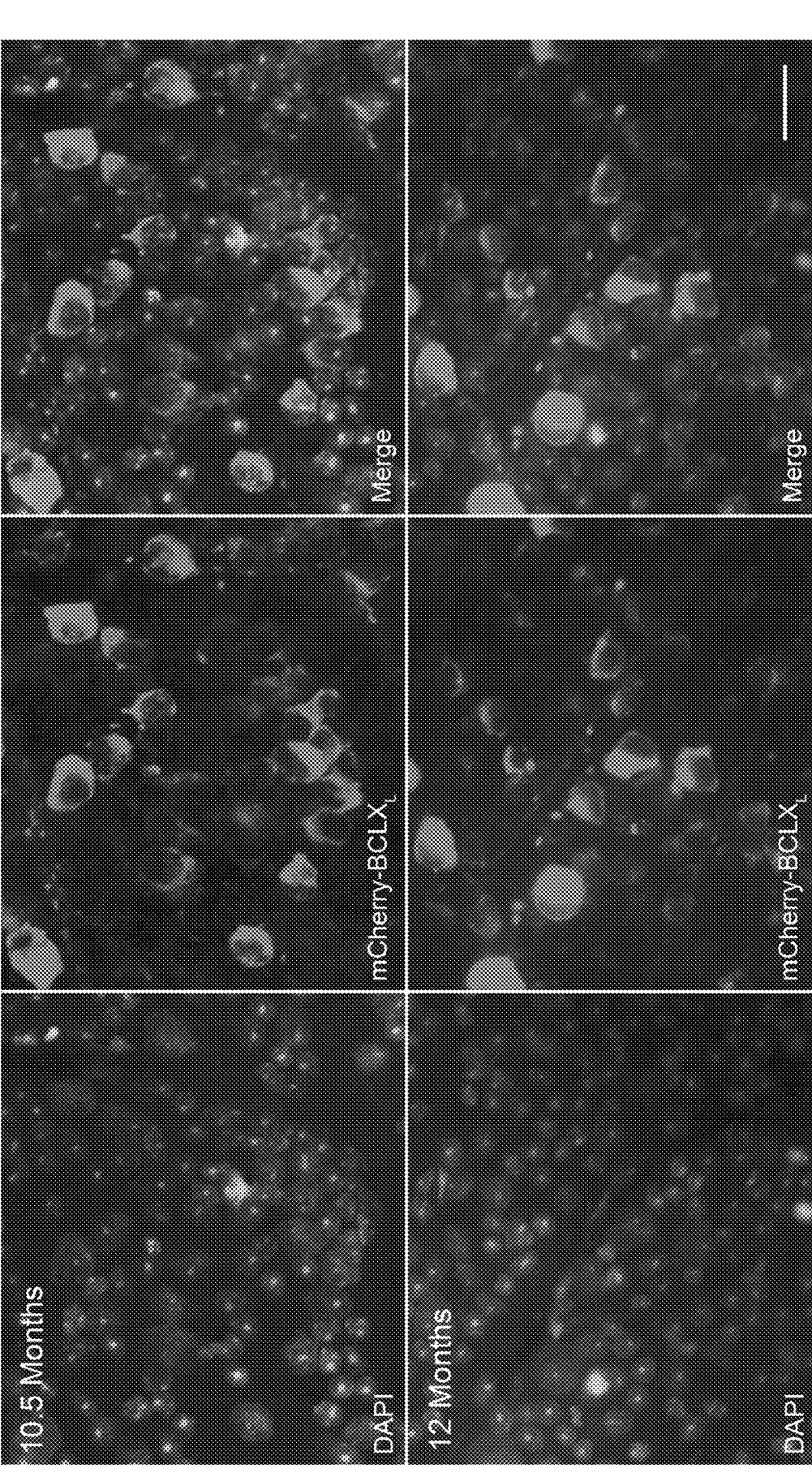

FIG. 10 shows images of whole mounted retinas showing mCherry-BCLX$_L$ expression in the ganglion cell layer of DBA/2J mice. Retina of a 10.5-month-old mouse (top panels) and 12-month-old mouse (bottom panels) showing cells with robust expression of the transgene. Individual channels are shown. Scale bar=20 µm.

Figure 11:
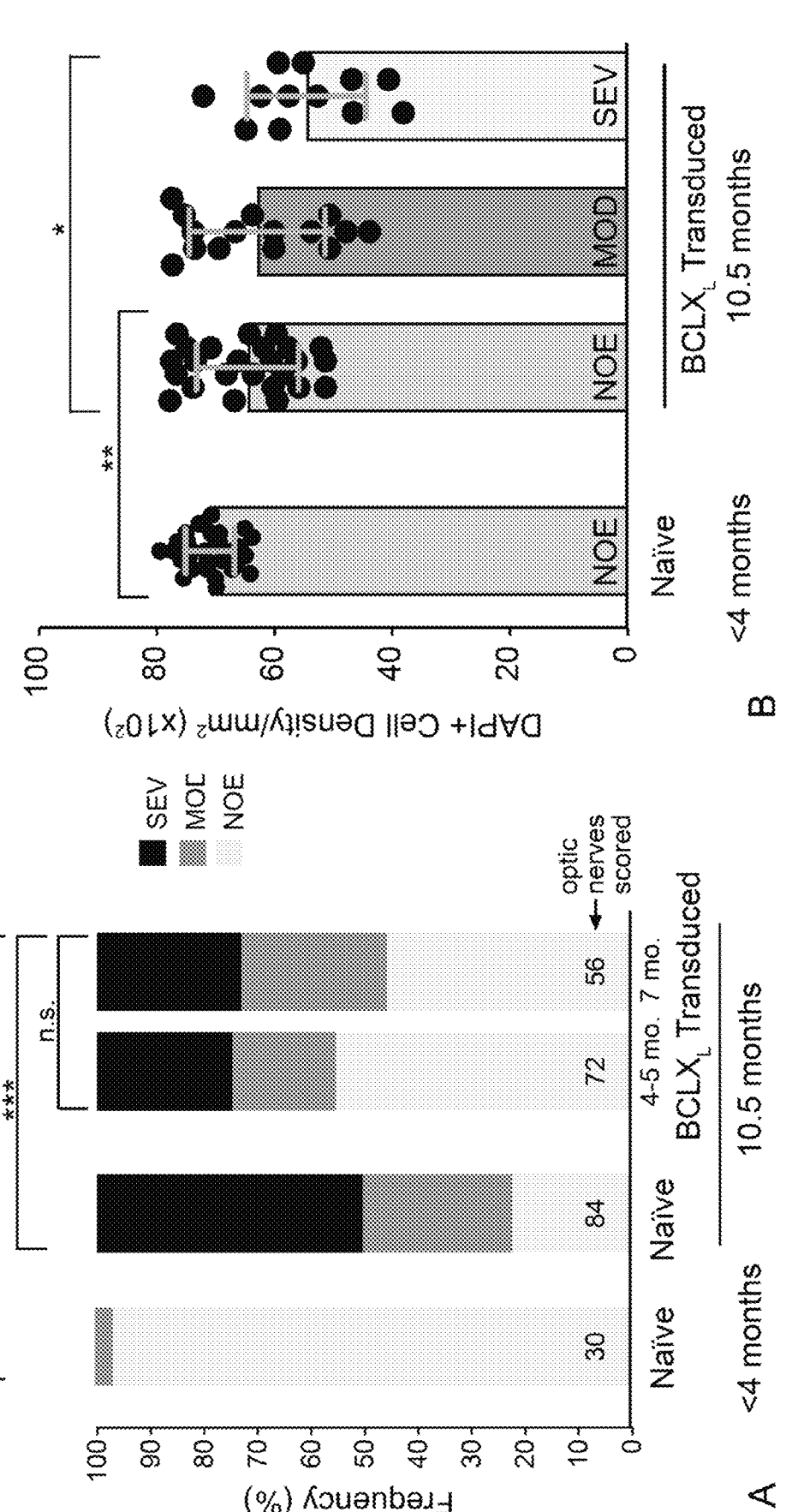

FIG. 11 shows glaucomatous damage scores in 10.5-month-old DBA/2J mice transduced at 7 months of age. A: Histographs of optic nerve scores. The data shown for young naïve mice (<4 months old), naïve mice at 10.5 months, and mice at 10.5 months treated with AAV2/2-Pgk-mCherry-BCLX$_L$ at 4-5 months of age are reproduced from FIG. 7. These data are compared to data from 10.5-month-old DBA/2J mice transduced with virus at 7 months of age. Statistical comparisons are only shown for the 7-month treated group relative to the other cohorts (statistics for the other groups are shown in FIG. 7). The distribution of mice for each cohort (M/F) was: <4 (4/12); 10.5 Naïve (21/21); 10.5 (transduced at 4-5 mo.) BCLX$_L$ (22/15); 10.5 (transduced at 7 mo.) BCLX$_L$ (12/16). $\chi^2$ tests, n.s.=not significant, *P<0.0001. B: Scatter plot showing total retinal cell density as a function of optic nerve score. The data for <4-month-old mice is reproduced from FIG. 8**. The distribution of mice transduced at 7 months was 10 male and 16 female. Student t-tests, *P=0.0035, **P=0.001.

Figure 12:
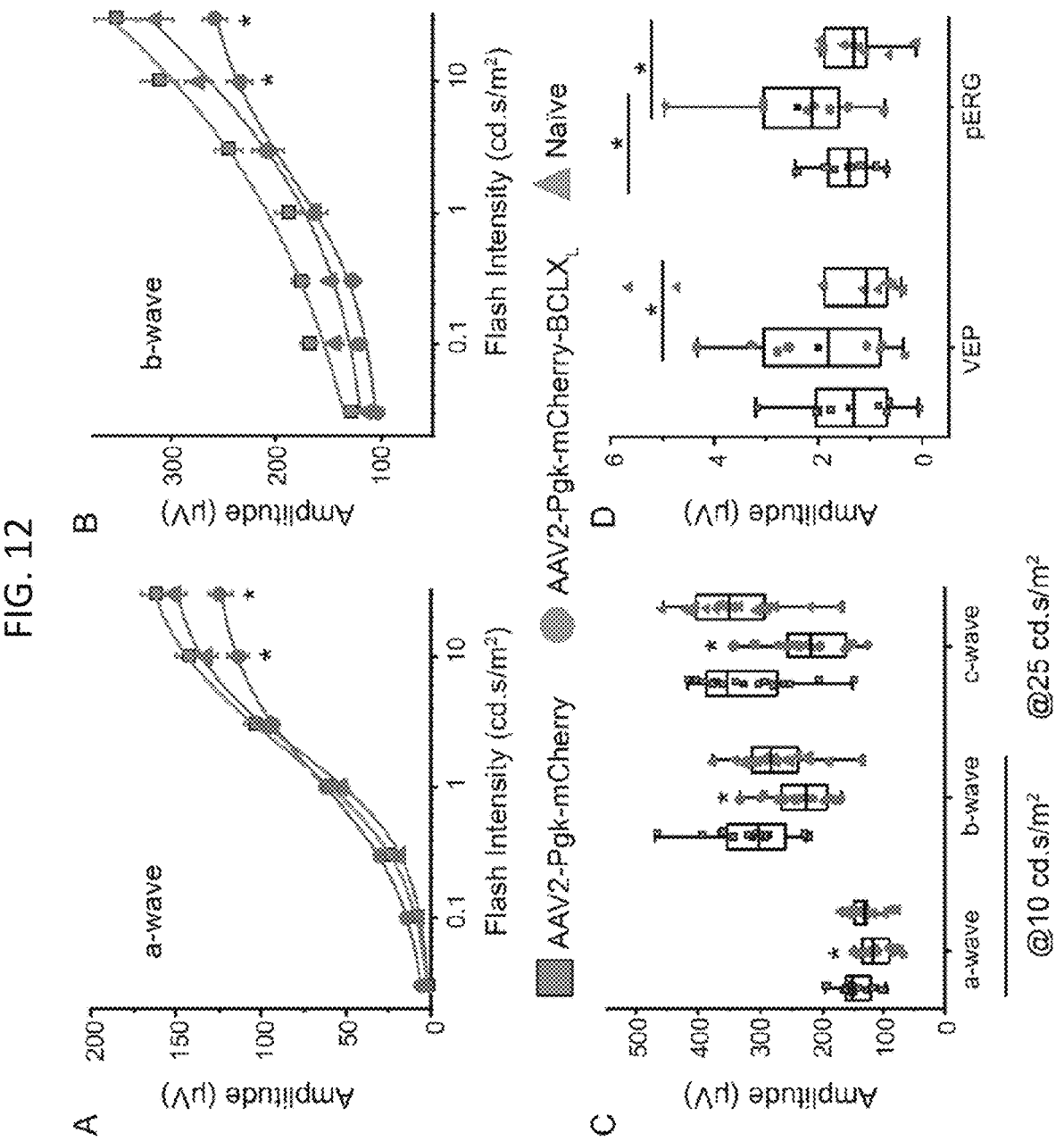

FIG. 12 shows that mCherry-BCLX$_L$ protects visual function in glaucomatous mice. Visual function testing was performed on mice treated with virus containing mCherry (AAV2-Pgk-mCherry), mice treated with virus containing the mCherry-BCLX$_L$ transgene (AAV2-Pgk-mCherry-BCLX$_L$), and aged naïve mice. Mice were injected with virus at 2.5 months of age and assessed for function using visual evoked potential (VEP), scotopic flash electroretinogram (ERG), and pattern ERG (pERG) testing at >10 months. (A-C) Graphs showing the results of ERG testing. (D) Graph showing the results of VEP and pERG testing.

DETAILED DESCRIPTION

The present invention provides vectors for delivery of an anti-apoptotic therapy. The vectors include a phosphoglycerate kinase (Pgk) promoter operably connected to a polynucleotide encoding an anti-apoptotic BCL2 protein (e.g., BCLX$_L$). The vectors may be used in methods of treating conditions associated with apoptosis, such as glaucoma.
Glaucoma:

Glaucoma is an optic neuropathy that is characterized by degeneration of the optic nerve and retinal ganglion cell (RGC) bodies in the innermost region of the sensory retina. RGCs are long projection neurons of the central nervous system. They acquire sensory input from the other neurons of the sensory retina and transmit those signals through their axons to visual centers in the brain. The axons of RGCs extend out of the retina and into the optic nerve. In humans, dogs, and cats, RGC axons from one eye split at the optic chiasm, with 50% (humans), 75% (dogs), or 65% (cats) of them crossing at the chiasm and projecting ipsilaterally. The principal target for RGC axons in these animals is the lateral geniculate nucleus. In mice, 95% of the RGC axons cross at the chiasm, with the majority of them projecting to the superior colliculus.

The pathophysiology of glaucoma is only partially understood at this point. The major risk factor for glaucoma is the elevation of intraocular pressure (IOP) above normal levels. It is important to note, however, that elevated IOP (i.e., ocular hypertension, defined as IOP levels above the median of a population) is not glaucoma, although there is a clear continuum that links ocular hypertension with the onset of the disease. Approximately 10% of individuals who develop ocular hypertension will develop glaucoma. Additionally, glaucoma can develop in individuals who have normal, or below normal, IOP levels (called normal tension glaucoma). These individuals develop clinical pathology associated with glaucoma, including cupping of the optic nerve head, thinning of the nerve fiber layer, and the development of glaucoma-characteristic scotomas in visual field exams.

Indicative of the continuum between IOP and glaucoma, lowering IOP in patients with normal tension glaucoma, has a beneficial effect of slowing the progression of the optic neuropathy. Some people with ocular hypertension clearly have a greater threshold for the damage induced by IOP changes, while the threshold is likely much lower in individuals who develop normal tension glaucoma. Importantly, the current treatment of all forms of glaucoma is limited to lowering IOP with medicines or surgical intervention. While this treatment serves to slow the rate of progression of disease, it does not stop the degenerative process. New efforts to directly target the RGCs and their axons with a therapeutic are expected to dramatically improve the rates of vision preservation in the treatment of glaucoma, especially if used adjunctively with conventional IOP-lowering therapies. This could have an important economic impact on healthcare costs worldwide, as glaucoma is already the most prevalent neurodegenerative disease, and its prevalence is expected to rapidly increase in the next two decades due to the aging population.

The pathophysiology of glaucoma is rooted in strain generated by IOP on the region of the eye where RGC axons exit and enter the optic nerve (i.e., the optic nerve head). Biomechanical engineers have modeled tissue structures to help define this region as the most susceptible to changes in IOP, and it is suspected that this strain initiates changes in tissue structure that have the unintended consequence of altering metabolic support to the axons in this region. A direct consequence of ocular hypertension is the blockage of both anterograde and retrograde transport in RGC axons. The decrease in anterograde transport is thought to limit essential materials required for axon maintenance and integrity, causing a progressive degeneration from the synapse to the cell soma. The loss of retrograde transport blocks the flow of essential trophic factors that are released by target neurons in the brain. It is thought that these factors signal to RGCs that they still have appropriate contact with their downstream target neurons. Loss of these factors affects Akt/phosphoinositol 3-kinase signaling in the retina, stimulating a new signaling cascade leading to the activation of apoptotic death. Extensive investigation has identified the dual leucine zipper kinase (DLK)-Jun N-terminal kinase (JNK) signaling axis as the principal pathway in this cascade, but it is important to note that several secondary and overlapping signaling pathways appear to be involved.

Further studies have determined that intrinsic apoptosis is the principal mechanism of RGC death in nearly all forms of optic nerve damage, including glaucoma. Intrinsic apoptosis involves mitochondrial dysfunction and is universally controlled by members of the BCL2 gene family. The BCL2 gene family contains three functionally distinct groups of proteins, which are all related by a similar amino acid sequence called the BCL2 homology 3 (BH3) domain. There are numerous members of proteins in each group, but only the members that are predominantly expressed in RGCs will be discussed. With respect to anti-apoptotic function, RGCs normally express the long form of BCLX (BCL2L1, referred to herein as BCLX$_L$) from this family. With respect to dominant pro-apoptotic function, RGCs express BAX (BCL2L4).

The importance of the interaction of BCLX$_L$ and BAX in the process of RGC death has been mostly studied in mice in which these genes have been genetically manipulated. Transgenic mice overexpressing the BCLX$_L$ homolog (BCL2) exhibit profound protection of RGC somas in the retina after acute transection of the optic nerve. Similarly, mice with the Bax gene deleted exhibit complete preservation of RGC somas in models of both acute (optic nerve crush) and chronic (inherited glaucoma in the DBA/2J strain of mouse) optic nerve damage. Additionally, in DBA/2J glaucoma, absence of the Bax gene provided significant, but transient preservation of axons in the optic nerve. To date, deletion of the Bax gene has been the only experimental condition that completely abrogates RGC soma death in models of optic nerve damage. This phenomenon underscores the likelihood that the activation of BAX represents the rate limiting step in the pathology of RGCs.

Previous studies suggest that forced expression of anti-apoptotic proteins such as BCL2 or BCLX$_L$ in cells alters the balance between the anti-apoptotic proteins and the sum accumulation of BH3-only proteins. Sufficient levels of anti-apoptotic proteins are still present to continue to antagonize BAX even after cell death signaling has been initiated. The ability of this approach to protect RGCs after acute optic nerve damage was documented using a transgenic mouse expressing human BCL2 under control of a neuronal promoter. However, a single attempt to introduce BCLX$_L$ into RGCs using recombinant adeno-associated virus (genome serotype 2, capsid serotype 2—AAV2/2)-mediated gene delivery was met with limited success in an acute rodent model of optic nerve damage. One challenge of this approach has been the choice of an appropriate promoter to drive gene expression in RGCs. This is particularly true in cells that have experienced damage, as the damage response of RGCs is to silence genes that are not required for subsequent steps in the cell death program.

As is described in the Examples, the inventors have overcome this challenge by using the glycolytic enzyme phosphoglycerate kinase (Pgk) promoter. The inventors demonstrate that this promoter can be used to efficiently drive transgene expression in damaged RGCs. Specifically, they generated an AAV2/2 vector in which this promoter is used to drive the expression of BCLX$_L$, and they showed that this vector can be used as a therapeutic intervention to prevent glaucomatous neurodegeneration and limit optic nerve damage.

Vectors:

In a first aspect, the present invention provides vectors comprising a phosphoglycerate kinase (Pgk) promoter operably connected to a polynucleotide encoding an anti-apoptotic BCL2 protein. The Pgk promoter comprises SEQ ID NO:1 (i.e., the mouse Pgk-1 promoter), SEQ ID NO:2 (i.e., the human Pgk-1 promoter), or a sequence having 80% identity to SEQ ID NO:1 or SEQ ID NO:2. In some embodiments, the Pgk promoter comprises a sequence that is 85%, 90%, 91%, 92%, 93%, 94%, 95%, 96%, 97%, 98%, 99%, or 100% identical to SEQ ID NO:1 or SEQ ID NO:2.

The term "vector" refers to a nucleic acid molecule capable of propagating another nucleic acid to which it is linked. The term includes the vector as a self-replicating nucleic acid structure as well as the vector incorporated into the genome of a host cell into which it has been introduced. Certain vectors, referred to as "expression vectors", are capable of directing the expression of nucleic acids to which they are operatively linked. Vectors suitable for use with the present invention comprise the polynucleotide encoding an anti-apoptotic BCL2 protein and heterogeneous sequence necessary for proper propagation of the vector and expression of the encoded protein.

In some embodiments, the vector is viral vector. A viral vector may be a virus particle or may be encoded on a DNA plasmid. In embodiments in which the viral vector is a virus particle, the virus particle may include a VSV-G envelop protein. The abilities of certain viral vectors to efficiently infect or enter cells, to integrate into a host cell genome, and to stably express viral genes, have led to the development of viral vector systems for use in ex vivo and in vivo gene transfer. For example, adenovirus, herpes-simplex virus, retrovirus, and adeno-associated virus vectors are being evaluated for treatment of human diseases. Suitable viral vectors for use with the present invention include, without limitation, retroviral vectors (e.g., lentiviral vectors), adeno-associated viral (AAV) vectors, adenoviral vectors, and herpes-simplex vectors.

In the Examples, the inventors packaged their protein using adeno-associated virus (AAV), a member of the parvovirus family. Thus, in some embodiments, the vector is an adenovirus associated viral vector. AAV is a human virus that is increasingly being used for gene delivery therapeutics because it has several advantageous features not found in other viral systems. First, AAV can infect a wide range of host cells, including non-dividing cells. Second, AAV can infect cells from different species. Third, AAV has not been associated with any human or animal disease and does not appear to alter the biological properties of the host cell upon integration. Finally, AAV is stable in a wide range of physical and chemical conditions, which makes it amenable to a variety of production, storage, and transportation requirements.

The AAV genome is a linear, single-stranded DNA molecule containing 4681 nucleotides. The AAV genome generally comprises an internal non-repeating genome flanked on each end by inverted terminal repeats (ITRs) of approximately 145 bp in length. The internal portion of the genome includes two large open reading frames, known as the AAV replication (rep) and capsid (cap) genes. The rep and cap genes code for viral proteins that allow the virus to replicate and package the viral genome into a virion. The ITRs flanking the internal portion of the genome function as origins of DNA replication and as packaging signals for the viral genome. AAV ITRs may be derived from any AAV genome serotype, including from AAV1, AAV2, AAV3, AAV4, AAV5, AAV6, AAV7, AAV8, AAV9, AAV10, AAV11, avian AAVs, and bovine AAVs. The 5' and 3' ITRs used in the AAV viral vectors need not be identical or derived from the same AAV serotype. For example, both (1) homologous vectors comprising an expression cassette flanked by AAV2-ITRs and packaged in an AAV2 capsid, and (2) heterologous hybrid vectors comprising an expression cassette flanked by AAV2 ITRs and packaged using a capsid that originates from another AAV serotype (e.g., AAV5) can be produced. In the Examples, the inventors demonstrate that an AAV viral vector of genome serotype 2 and capsid serotype 2 (i.e., AAV2/2) can be used to effectively deliver expression constructs into cells. Thus, in some embodiments, the vector comprises an AAV2 vector. In specific embodiments, the AAV2 vector is an AAV2/2 vector.

AAV is a helper-dependent virus, meaning that it requires co-infection with a helper virus (e.g., an adenovirus, herpesvirus, or vaccinia helper virus) to form AAV virions. In the absence of a helper virus, AAV establishes a latent state in which the viral genome inserts into a host cell genome, but infectious virions are not produced. Subsequent infection by a helper virus "rescues" the integrated viral genome, allowing it to replicate and be packaged into infectious AAV virions. Although AAV can infect cells from different species, the helper virus must be of the same species as the host cell (e.g., human AAV will replicate in canine cells co-infected with a canine adenovirus).

AAV is engineered to deliver genes of interest by deleting the internal non-repeating portion of the AAV genome and inserting a heterologous gene between the ITRs. The heterologous gene may be functionally linked to a heterologous promoter that is capable of driving gene expression in target cells. To produce infectious, recombinant AAV (rAAV) containing a heterologous gene, a suitable producer cell line is transfected with a rAAV vector containing the heterologous gene. The producer cell is concurrently transfected with a second plasmid harboring the AAV rep and cap genes under the control of their respective endogenous promoters or heterologous promoters. Finally, the producer cell is infected with a helper virus. Once these factors come together, the heterologous gene is replicated and packaged as though it were a wild-type AAV gene. When target cells are infected with the resulting rAAV virions, the heterologous gene enters and is expressed in the target cells. However, because the target cells lack the rep, cap, and adenovirus helper genes, the rAAV cannot replicate or form AAV virions in the hose cell.

Because AAV has a single-stranded DNA genome, double-stranded DNA must first be generated to allow for transcription and translation of the heterologous gene. This process can slow production of the heterologous protein after vector delivery to cells. To expedite expression from delivered polynucleotides, the AAV vector can be engineered such that the delivered genetic material is self-complementary. As used herein, the term "self-complementary" refers to a single-stranded DNA that contains at least two portions that are complementary to each other, such that these portions hybridize and form double-stranded DNA. Thus, in some embodiments, the vector is a self-complementary single-stranded DNA.

As used herein, the term "promoter" refers to a DNA sequence that regulates the expression of a gene. Typically, a promoter is a regulatory region that is capable of binding RNA polymerase and initiating transcription of a downstream (3' direction) sequence. However, a promoter may be located at the 5' or 3' end, within a coding region, or within an intron of a gene that it regulates. Promoters may be derived in their entirety from a native gene, may be composed of elements derived from multiple regulatory sequences found in nature, or may comprise synthetic DNA segments. It is understood by those skilled in the art that different promoters may direct the expression of a gene in different tissues or cell types, at different stages of development, or in response to different environmental conditions. A promoter is "operably connected" to a polynucleotide if the promoter is connected to the polynucleotide such that it may affect transcription of the polynucleotide.

The vectors of the present invention comprise the phosphoglycerate kinase (Pgk) promoter. This promoter was selected based on previous studies showing that retinal ganglion cells (RGCs) downregulate expression from many neuron-specific promoters and poorly utilize the CMV immediate early promoter after they become damaged [30]. This loss of expression can be circumvented by using the Pgk promoter, whose expression is sustained in damaged RGCs [31]. In some embodiments, the Pgk promoter comprises SEQ ID NO:2.

The vectors of the present invention are gene therapy vectors that are designed to express an anti-apoptotic BCL2 protein in a target cell. The BCL2 protein family is divided into three groups based on primary function: (1) anti-apoptotic proteins (e.g., BCLX$_L$), (2) pro-apoptotic pore-forming proteins (e.g., BAX), and (3) pro-apoptotic BH3-only proteins. Suitable anti-apoptotic BCL2 proteins for use with the present invention include, without limitation, BCL2, BCLX, BCLW, MCL1, and BFL1/A1. In some embodiments, the anti-apoptotic BCL2 protein is selected from murine BCLX (DNA sequence: SEQ ID NO:7, amino acid sequence: SEQ ID NO:8), feline BCLX (DNA sequence: SEQ ID NO:9, amino acid sequence: SEQ ID NO:10), canine BCLX (DNA sequence: SEQ ID NO:11, amino acid sequence: SEQ ID NO:12), canine BCL2 (DNA sequence: SEQ ID NO:13, amino acid sequence: SEQ ID NO:14), human BCLX$_L$ (DNA sequence: SEQ ID NO:15, amino acid sequence: SEQ ID NO:16), human BCL2 (DNA sequence: SEQ ID NO:17, amino acid sequence: SEQ ID NO:18), human BCLW (DNA sequence: SEQ ID NO:19, amino acid sequence: SEQ ID NO:20), or sequences 80% identical thereto. In preferred embodiments, the anti-apoptotic BCL2 protein comprises SEQ ID NO:16 (i.e., human BCLX$_L$). In some embodiments, the BCL2 protein comprises a sequence that is 85%, 90%, 91%, 92%, 93%, 94%, 95%, 96%, 97%, 98%, 99%, or 100% identical to a sequence selected from SEQ ID NOs:8, 10, 12, 14, 16, 18, and 20.

The term "polynucleotide" refers a polymer of DNA or RNA. A polynucleotide may be single-stranded or double-stranded, synthesized, or obtained (e.g., isolated and/or purified) from a natural source. A polynucleotide may contain natural, non-natural, or altered nucleotides, as well as natural, non-natural, or altered internucleotide linkages (e.g., a phosphoroamidate linkage or a phosphorothioate linkage). The term polynucleotide encompasses constructs (i.e., artificially constructed DNA molecules), plasmids, vectors, and the like.

The terms "protein", "polypeptide", or "peptide" are used interchangeably herein to refer to a polymer of amino acids. A polypeptide typically comprises a polymer of naturally occurring amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine).

Regarding the polypeptides described herein, the phrases "% sequence identity," "percent identity," or "% identity" refer to the percentage of residue matches between at least two amino acid sequences aligned using a standardized algorithm. Methods of amino acid sequence alignment are well-known. Some alignment methods take into account conservative amino acid substitutions. Conservative substitutions generally preserve the charge and hydrophobicity at the site of substitution, thus preserving the structure (and therefore function) of the polypeptide. Percent identity for amino acid sequences may be determined as understood in the art. See, e.g., U.S. Pat. No. 7,396,664, which is incorporated herein by reference in its entirety. A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases. Polypeptide sequence identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 10, at least 15, at least 20, or more contiguous residues. Such lengths are exemplary only, and it is understood that any fragment length supported by the sequences shown herein, in the tables, figures or Sequence Listing, may be used to describe a length over which percentage identity may be measured.

Pharmaceutical Compositions:

In a second aspect, the present invention provides pharmaceutical compositions comprising a vector disclosed herein and a pharmaceutically acceptable carrier.

A "pharmaceutically acceptable carrier" is a carrier, excipient, or diluent, that is nontoxic to the cell or subject being exposed thereto at the dosages and concentrations employed. Many pharmaceutically acceptable carriers are known in the art and include, but are not limited to, water, buffers (e.g., phosphate, citrate, and other organic acids), diluents (e.g., Tris-HCl, acetate, phosphate), preservatives (e.g., Thimerosal, benzyl alcohol, parabens), solubilizing agents (e.g., glycerol, polyethylene glycerol), emulsifiers, liposomes, nanoparticles, and adjuvants. Pharmaceutically acceptable carriers may be aqueous or non-aqueous solutions, suspensions, or emulsions. Examples of nonaqueous solvents are propylene glycol, polyethylene glycol, vegetable oils such as olive oil, and injectable organic esters such as ethyl oleate. Aqueous carriers include isotonic solutions, alcoholic/aqueous solutions, emulsions, or suspensions, including saline and buffered media. Often a pharmaceutical carrier is in an aqueous pH buffered solution.

The pharmaceutical compositions of the present invention may further include additives such as albumin or gelatin to prevent absorption to surfaces, detergents (e.g., Tween 20, Tween 80, Pluronic F68, bile acid salts), antioxidants (e.g., ascorbic acid, sodium metabisulfite), bulking substances, or tonicity modifiers (e.g., lactose, mannitol). Components of the compositions may be covalently attached to polymers (e.g., polyethylene glycol), complexed with metal ions, or incorporated into or onto particulate preparations of polymeric compounds (e.g., polylactic acid, polyglycolic acid, hydrogels, etc.) or onto liposomes, microemulsions, micelles, bilamellar or multilamellar vesicles, erythrocyte ghosts, or spheroplasts. The compositions may also be formulated in lipophilic depots (e.g., fatty acids, waxes, oils) for controlled or sustained release.

Injectable preparations (e.g., sterile injectable aqueous or oleaginous suspensions) are formulated according to the known art using suitable dispersing or wetting agents and suspending agents. The injectable preparation may comprise a solution, suspension or emulsion in a nontoxic parenterally acceptable diluent or solvent. For this purpose, any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of solid compositions, which can be dissolved or dispersed in sterile water or other sterile injectable medium prior to use.

Methods:

In a third aspect, the present invention provides methods of treating a subject having a condition associated with apoptosis of a cell. The methods comprise administering a therapeutically effective amount of any one of the vectors or pharmaceutical compositions disclosed herein to the subject.

The "subject" to which the methods are applied may be a mammal or a non-mammalian animal, such as a bird. Suitable mammals include, but are not limited to, humans, cows, horses, sheep, pigs, goats, rabbits, dogs, cats, bats, mice, and rats. In certain embodiments, the methods may be performed on lab animals (e.g., mice and rats) for research purposes. In other embodiments, the methods are used to treat commercially important farm animals (e.g., cows, horses, pigs, rabbits, goats, sheep, and chickens) or companion animals (e.g., cats and dogs). In preferred embodiments, the subject is a human.

As used herein, a "condition associated with apoptosis of a cell" refers to a disease or condition in which aberrant apoptosis leads to a defect or disease, and which can be treated by blocking or inhibiting apoptosis. Such conditions include, but are not limited to, glaucoma, multiple sclerosis, hereditary optic neuropathy, traumatic optic nerve injury, ischemic/reperfusion injury of the retina, anterior ischemic optic neuropathy, and other neurodegenerative conditions.

In the Examples, the inventors demonstrate that their $BCLX_L$ gene therapy can be used to prevent axonal degeneration in the retina and optic nerve of a mouse model of glaucoma. Thus, in preferred embodiments, the condition is glaucoma. The term "glaucoma" includes all forms of glaucoma and diseases associated with increased intraocular pressure including, but not limited to, primary open angle glaucoma, angle closure glaucoma, normal tension glaucoma, pigmentary glaucoma, congenital glaucoma, and exfoliation glaucoma.

As used herein, "treating" or "treatment" describes the management and care of a subject for the purpose of combating a disease, condition, or disorder. Treating includes any treatment that prevents or delays the onset of the symptoms or complications, alleviates the symptoms or complications, delays the progression of the disease, or eliminates the disease, condition, or disorder. More specifically, treating includes, but is not limited to, reducing the number of cells undergoing apoptosis, reducing or slowing the progression of a degenerative disease, limiting the loss of vision in glaucoma, or slowing or limiting the loss of cells after a traumatic injury.

The vectors and pharmaceutical compositions described herein may be administered to the subject by any means known to those skilled in the art including, without limitation, intraocularly, topically, intranasally, intramuscularly, or subcutaneously.

In some embodiments, the targeted tissue is ocular. For example, in some embodiments, the target cells are retinal cells. In specific embodiments, the retinal cells are retinal ganglion cells. In embodiments in which the targeted tissue is ocular, the vectors and pharmaceutical compositions can be administered to the eye of a subject by several routes including trans-ocular, intravitreal, topical, trans choroidal, intracameral, supra choroidal, transdermal, subretinal, intraperitoneal, subcutaneous, and intravenous routes. In the Examples, the inventors delivered their vectors to the eyes of mice intraocularly, i.e., via intravitreal injection. Thus, in some embodiments, the vector is administered intraocularly. In specific embodiments, the intraocular administration is via intravitreal injection.

The term "therapeutically effective amount" refers to an amount that is sufficient to effect beneficial or desirable biological or clinical results. That result can be reducing, alleviating, inhibiting, or preventing one or more symptoms of a disease or condition. The therapeutically effective amount will vary depending on the composition being administered, the timing and mode of administration, the condition being treated and its severity, and the age, weight, physical condition, diet, and responsiveness of the subject to be treated. Thus, the exact dosage should be chosen by a physician in view of these variables. For any active agent, a therapeutically effective amount can be estimated initially in cell culture assays or in animal models, usually mice, rabbits, dogs, cats, or pigs. A suitable dosage for a specific subject can be determined using conventional considerations, e.g., by comparison of the differential activities of the compositions described herein and of a known agent using a pharmacological or prophylactic protocol. The term therapeutically effective amount refers to the total amount administered, as the compositions can be administered as a single dose or as divided doses. For example, the composition may be administered two or more times separated by 4 hours, 6 hours, 8 hours, 12 hours, a day, two days, three days, four days, one week, two weeks, or by three or more weeks.

In some embodiments, the vectors and pharmaceutical compositions are administered based on the number of copies of the vector encoding the anti-apoptotic polypeptide that are delivered to the subject. For example, the subject may be administered between $10^8$ and $10^{14}$, or between $10^9$ and $10^{12}$, or between $10^9$ and $10^{11}$ copies of the vector. In embodiments where the gene therapy vector is a viral vector, the subject may be administered between $10^8$ and $10^{14}$, or between $10^9$ and $10^{12}$, or between $10^9$ and $10^{11}$ viral genomes.

The methods provided herein may further include administering an additional therapeutic or a surgical intervention. The additional therapeutic may be useful for treating either the same condition as the vector or a different condition. In embodiments in which the treated condition is glaucoma, the methods may further comprise administering a therapeutically effective amount of a glaucoma therapeutic. The glaucoma therapeutic may be a prostaglandin or prostaglandin analog, a beta blocker, an alpha agonist, a carbonic anhydrase inhibitor, a rho kinase inhibitor, or combinations thereof. Examples of such therapeutics include, but are not limited to, latanoprost, bimatoprost, travoprost, tafluprost, latanoprostene, timolol, brimonidine, dorzolamide, brinzolamide, acetazolamide, methazolamide, and netarsudil. Many glaucoma therapeutics and surgical interventions are directed towards lowering intraocular pressure.

The vector and the additional therapeutic may be administered in any order, at the same time, or as part of a unitary composition. The vector and the additional therapeutic may be administered such that one is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks, or more. For the treatment of glaucoma, the vector may be administered via intraocular administration such as intravitreal administration and the glaucoma therapeutic may be administered as eye drops or an oral therapeutic before, at the same time, after, or continuously throughout the administration of the vector.

In the Examples, the inventors demonstrate that administration of their BCLX$_L$ gene therapy (1) prevents cell loss in the retinal ganglion cell layer in mice following acute optic nerve damage (i.e., optic nerve crush), (2) prevents retinal ganglion cell degeneration in a mouse model of glaucoma, and (3) protects visual function in a mouse model of glaucoma. Thus, in some embodiments, administration of the vector to an eye of the subject reduces retinal ganglion cell loss after traumatic optic nerve damage in the eye as compared to a control subject not receiving the vector. In other embodiments, administration of the vector to an eye of a subject with glaucoma reduces retinal ganglion cell degeneration as compared to a control subject not receiving the vector. In other embodiments, administration of the vector to an eye of a subject with glaucoma reduces the loss of visual function as compared to a control subject not receiving the vector. As used herein, the term "control subject" refers to a comparable subject (e.g., of the same species, sex, and age) that was not administered the vector.

Retinal ganglion cell loss and degeneration can be evaluated post-mortem in an experimental model (e.g., a rodent). To prepare optic nerves for analysis, they are isolated, fixed, and embedded in Epon plastic and thick (1 μm) sections are cut and stained to visualize myelin sheathes. Retinal ganglion cell loss can then be detected via (1) a direct quantitative assessment of RGC number obtained by counting intact remaining axons, or (2) an analysis of total neuronal cell density. Retinal ganglion cell degeneration can be evaluated by scoring nerve sections for myelin-whorls, loss of axons, and the presence of glial scar tissue. In the retina, degeneration can be assessed using (1) a summary count of the density of the entire neuronal population in the ganglion cell layer (which includes both RGCs and amacrine cells), (2) stains for markers of RGCs (which includes TUBB3, RBPMS, and BRN3 homologs), or (3) stains for markers of apoptosis, such as activated caspase 3, phosphorylated JUN transcription factor, or DNA fragmentation (i.e., TUNEL).

Changes in visual function that are also associated with neurodegeneration can be assessed using a variety of tests. Common tests used for rodents include the optimotor response (OMR) test and water maze testing. In humans, loss of visual function can be assessed using visual field (VF) testing (e.g., using a Goldmann Visual Field/Kinetic Perimetry Test). However, since detection of visual field defects using this test is often indicative of late vision loss, VF testing can be augmented using spectral domain optical coherence testing (SD-OCT), which measures the thickness of the nerve fiber layer in optic sections of the retina and can detect neurodegenerative changes that precede the formation of defects in a VF exam. In both rodents and humans, visual function can also be assessed using electrophysiological methods. Suitable electrophysiological methods include visual evoked potential, which measures electrical conductance from the eye to the brain, and pattern electroretinography (pERG), which measures the retinal electrical response to a moving pattern of black and white bars.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

Axonal degeneration of retinal ganglion cells (RGCs) causes blindness in glaucoma. Currently, there are no therapies that target axons to prevent them from degenerating. Activation of the BAX protein has been shown to be the determining step in the intrinsic apoptotic pathway that causes RGCs to die in glaucoma. A putative role for BAX in axonal degeneration is less well elucidated. $BCLX_L$ (BCL2L1) is the primary antagonist of BAX in RGCs. We developed a mCherry-$BCLX_L$ fusion protein, which prevented BAX recruitment and activation to the mitochondria in tissue culture cells exposed to staurosporine. This fusion protein was then packaged into adeno-associated virus serotype 2, which was used to transduce RGCs after intravitreal injection and force its overexpression. Transduced RGCs express mCherry-$BCLX_L$ throughout their somas and axons along the entire optic tract. In a model of acute optic nerve crush, the transgene prevented the recruitment of a GFP-BAX fusion protein to mitochondria and provided long-term somal protection up to 12 weeks post injury. To test the efficacy in glaucoma, DBA/2J mice were transduced at 5 months of age, just prior to the time they begin to exhibit ocular hypertension. Gene therapy with mCherry-$BCLX_L$ did not affect the longitudinal history of intraocular pressure elevation compared to naive mice but did robustly attenuate both RGC soma pathology and axonal degeneration in the optic nerve at both 10.5 and 12 months of age. Thus, $BCLX_L$ gene therapy is a promising candidate treatment for glaucoma.

Evidence suggests that RGC axons are injured early in glaucoma and can degenerate independently of the soma [3]. Mechanisms of axon degeneration have been an area of intense study for the past two decades. There is evidence for axon degeneration pathways mediated independently by SARM1 [3-5] and BAX [6-9]. In RGCs, BAX is essential for the execution of the caspase-dependent, intrinsic apoptotic program [6, 10, 11], but its role in glaucomatous axon degeneration is controversial [3, 5].

Bcl2l1 (hereafter designated as $BclX_L$) is an anti-apoptotic member of the Bcl2 gene family, and in central nervous system neurons is the primary antagonist of BAX [12]. $BCLX_L$ exists primarily at the mitochondria and inhibits BAX activation by preventing BAX from accumulating on the mitochondrial outer membrane [13]. Overexpression of $BCLX_L$ protects neurons from death following trophic factor withdrawal and ischemia-reperfusion [14-16]. In RGCs, increasing the intracellular concentration of $BCLX_L$ prevents the degeneration of somas and proximal axon segments after axotomy [17, 18].

The DBA/2J mouse is a widely used model of glaucoma that develops spontaneous, asynchronous elevation of IOP around 6 months of age that persists until the mice are nearly a year old [19-21]. This causes degeneration of RGCs and makes the DBA/2J mouse a useful model for studying glaucomatous neurodegeneration. Experimentally, the ages of 10.5 and 12 months are frequently used for assessing degeneration. Some therapeutic approaches are protective exclusively at 10.5 months of age [6, 22], whereas others are protective at both 10.5 and 12 months of age [23-25]. The differential effect of therapies is evidence that multiple axon degenerative pathways contribute to glaucomatous neurodegeneration. Intriguingly, deletion of the Bax gene conferred protection only at 10.5 months of age but deletion of Bim, a protein that is important for activating BAX in RGCs, protected optic nerves (ONs) at both 10.5 and 12 months of age, suggesting that the BCL2 family may mediate axon degeneration independent of BAX activity in RGCs [6, 24]. Notably, both complete Bax and Bim deletion also affected the elevation of IOP, which may have contributed to their protective effect.

Gene therapy is a clinically relevant therapeutic paradigm for treating retinal disease [26]. The premise of gene therapy is to deliver a therapeutic gene to a susceptible population of cells, generally via a viral vector such as a recombinant adeno-associated virus (AAV). AAVs have low immunogenicity, are replication deficient, and are not known to cause any human disease [27]. In mice, intravitreal delivery of AAV serotype 2 (AAV2) of a sufficient titer can transduce around 85% of RGCs [28].

Gene therapy targeted directly to RGCs to prevent BAX activation in a glaucoma model has never been attempted. This approach is clinically relevant and can be performed in wild-type mice that do not have the developmental abnormalities associated with Bax deletion [29]. A previous study investigated $BCLX_L$ gene therapy in a model of ON axotomy and achieved significant albeit transient protection of RGCs [18]. The transient nature of the protection may have been due to loss of expression of the transgene, which was expressed using a neuron-specific promoter. Neuron-specific gene expression is rapidly silenced in RGCs following ON injury [30]. Loss of expression can be circumvented by using the Pgk promoter, whose expression is sustained in damaged RGCs [31].

Materials and Methods:

Cloning mCherry-BclX$_L$

Moloney Murine Leukemia Virus Reverse Transcriptase (Promega, Madison, WI) and Oligo(dT)$_{15}$ Primer (Promega) were used to make cDNA from total RNA isolated from BALB/c mouse brain tissue. Polymerase chain reaction (PCR) was used to amplify the coding region of the BclX$_L$ transcript from the cDNA using the following primers 5'-AAATGTCTCAGAGCAACCGGGAGCTG-3' (SEQ ID NO:3) and 5'-CAGTGTCTGGTCACTTCCGACT-GAAGAG-3' (SEQ ID NO:4). This PCR product was ligated into the pGemT vector using T4 DNA Ligase (Promega). BclX$_L$, was amplified with XhoI and HindIII restriction sites using the following primers 5'-TGGCCGGCTCGAGAAATGTCTCAG-3' (SEQ ID NO:5) and 5'-GATTCAGTAAGCTTTCACTTCCGACT-GAAG-3' (SEQ ID NO:6). This PCR product was digested with XhoI and HindIII (Promega) and ligated into a pmCherry-C1 plasmid (Clontech, Mountain View, CA), with BclX$_L$, placed downstream of mCherry. Sequencing was performed to verify that BclX$_L$, had the proper sequence and was in frame with mCherry. The resulting plasmid includes the mouse BclX$_L$ coding sequence (SEQ ID NO:7) operably linked to the mouse PGK-1 promoter (SEQ ID NO:1).

Validation of mCherry-BCLX$_L$, In Vitro

D407 cells were grown in Dulbecco's modified Eagle media (DMEM) (Corning, Corning, NY) containing 3% (V/V) fetal bovine serum (Atlanta Biologicals, Norcross, GA) and 1% penicillin-streptomycin (V/V) (Thermo Fisher Scientific, Waltham, MA). The GFP-BAX and mitoBFP constructs have been previously described [32, 33].

D407 cells were nucleofected using a Lonza 4D nucleofector (Lonza, Basel, Switzerland) and treated 24 h later with 1 µM staurosporine (STS) (Alfa Aesar, Ward Hill, MA). Live cell imaging was performed using an Andor Revolution XD spinning disc confocal microscope (Andor, Belfast, UK) in a 37° C. imaging chamber. Images were taken every 3 min for 3.5 h during the experiment. Image analysis was performed using the Imaris 9.2.1 software (Oxford Instruments, Abingdon, UK). The significant differences in the distribution between groups were assessed using $\chi^2$ tests.

Viral Packaging

The mCherry-BclX$_L$ construct was digested using NheI and ApaI and ligated into a bridge vector created from AAV-Pgk-Cre (Addgene plasmid #24593) where the Cre coding region was replaced with a multiple cloning site containing unique NheI and ApaI sites.

Following viral packaging, AAV2-Pgk-mCherry-BclX$_L$, and AAV2-Pgk-GFP-Bax had titers of $1.7 \times 10^{13}$ and $2.3 \times 10^{12}$ viral genomes/mL, respectively.

Mouse Housing and Ethics

Mice were handled in accordance with the Association for Research in Vision and Ophthalmology's Statement for the Use of Animals in Ophthalmic and Vision Research. Mice were kept in microisolator cages on a 12-h light/dark cycle and fed a 4% fat diet. Sample sizes were estimated using power calculations (0.8, 20% effective difference) with historical variance estimates for the type of assay used. All data shown used sample sizes that exceeded the "N" estimated by power calculations. Animals were randomly distributed into treatment groups with effort to balance male to female ratios. For DBA/2J mouse experiments, the male:female ratio is specifically indicated for each cohort in the figure legends. Any animals that exhibited distress after inclusion in a cohort were removed from the study.

Optic Nerve Crush (ONC) and Intravitreal Injections

For all surgeries, mice were anesthetized with 16 mg/mL ketamine and 1.5 mg/mL xylazine. Eyes were anesthetized with 0.5% proparacaine hydrochloride. Postoperative discomfort was alleviated with 0.03 mg/mL buprenorphine.

Intravitreal injection of virus or 1% cholera toxin subunit B (Alexa-488) (CTB-488; Thermo Fisher) was performed as previously described [30]. For experiments requiring injection of multiple viruses, titers were equalized by mixing the viruses followed by a single injection. Four weeks were allowed for viral genome replication and transgene expression. ONC was performed as previously described using C57BL/6J mice.

DBA/2J Experiments and IOP Measurements Using Rebound Tonometry

Ten-week-old DBA/2J mice were bilaterally injected with AAV2-Pgk-mCherry-BCLX$_L$. An additional cohort of 10 uninjected DBA/2J mice was used as a naive control. Each cohort contained 5 male and 5 female mice. IOPs were measured every 2 weeks between 9 and 11 a.m. using a Tonolab rebound tonometer (Icare, Finland) as previously described [35]. Eyes that developed corneal abnormalities were excluded. Longitudinal IOP history was analyzed using Generalized Estimating Equation regression modeling (R, v4.0.5).

For experiments measuring ON degeneration, DBA/2J mice between 4 and 5 or 7 months of age were bilaterally transduced with AAV2-Pgk-mCherry-BclX$_L$. Naive mice received no injection. Each cohort of glaucomatous mice contained at least 49 ONs and 29 retinas. We did not use a control viral injection because other studies have found no effect on IOP progression or protection of RGCs by control AAVs [35, 36]. Because glaucomatous disease progresses asymmetrically in the eyes of DBA/2J mice [21], each eye/retina/ON was considered as an independent variable.

Euthanasia, Tissue Removal, and Fixation

Mice were euthanized with pentobarbital sodium and phenytoin sodium (Virbac, Westlake, TX) followed by cervical dislocation. Eyes were enucleated with a proximal piece of the ON attached and placed in 4% paraformaldehyde (PFA) in phosphate-buffered saline (PBS, 100 mM phosphate buffer with 150 mM NaCl, pH 7.4) for 1 h. For ONC experiments, mice were euthanized 1 week after ONC. For glaucoma studies, mice were euthanized at 10.5 or 12 months of age. Young DBA/2J cohorts consisted of mice <4 months of age.

Frozen Sectioning and Staining of Whole-Eye Sections

After fixation, a brief PBS washed was performed. Samples, including both retinas and ONs, were equilibrated in 30% sucrose in PBS overnight at 4° C. Samples were then frozen on dry ice in plastic molds using O.C.T. Compound (Scigen, Paramount, CA). In all, 8 µm sections were obtained.

Immunofluorescence was performed as previously described [30]. Mouse anti-BRN3A monoclonal antibody (MAB1585) (EMD Millipore, Temecula, CA) was used at a concentration of 1:50. Rabbit anti-mCherry polyclonal antibody (ab167453) (Abcam, Cambridge, UK) was used at a concentration of 1:500. The anti-mCherry antibody was only used to enhance the signal of the sections that were used to assess transduction efficiency. All other samples showed endogenous mCherry signal. Rabbit anti-calbindin antibody (SWANT, Marly, Switzerland) was used at a concentration of 1:1000. Goat anti-mouse immunoglobulin G (IgG) fluorescein isothiocyanate conjugated to FITC or Alexa488 and goat anti-rabbit IgG conjugated to Texas Red, Alexa594 or Alexa488 (Jackson Immunoresearch, West Grove, PA) were used at a concentration of 1:1000.

Transduction efficiency was calculated as the percentage of 4,6-diamidino-2-phenylindole (DAPI)-positive nuclei that had mCherry-BCLX$_L$ labeling in the adjacent cytosolic compartment and the percentage of BRN3A-positive nuclei that had adjacent mCherry-BCLX$_L$ labeling. One section from four transduced eyes was counted.

Imaging of the ON Tract

Euthanized mice were decapitated, and the heads were placed in 4% PFA for 24 h. The skullcap and brain were then dissected away, taking care to leave the optic tract intact. Imaging was performed on a Zeiss Discovery V8 Stereo fluorescent microscope (Zeiss, Oberkochen, Germany). Images were taken using the Zen blue software (Zeiss).

Whole Mounting of Retinas, Imaging, and Calculation of Nuclear Densities

Retinas were whole mounted as previously described using VECTASHIELD Antifade Mounting Medium containing DAPI (Vector Laboratories, Burlingame, CA). Imaging and quantification of cellular density were performed as previously described [30]. Counted nuclei were restricted to cells with nuclear morphology typical of neurons (round euchromatic appearance with prominent nucleoli). At least 29 retinas were counted for each group. Statistical significance was calculated using a one-sided t test, which assumed equal variance between groups.

Quantitative PCR (qPCR)

Retinas that were used for qPCR were flash frozen in microcentrifuge tubes on dry ice. cDNA was created as previously described [30]. qPCR was performed using an ABI Quant Studio 7 RT PCR machine (Thermo Fisher Scientific). Primers for S16, BclX$_L$, Nefl, Nrn1, Thy1, Sncg, Tubb3, Gfap, Hsp27, and Gap43 have been described previously [37]. Absolute abundances of each transcript were calculated using a standard curve of S16 ribosomal protein mRNA [37]. Four groups of three pooled eyes were used for each experimental cohort. Statistical significance between the transcript abundances of different groups were calculated using a one-sided t test assuming equal variance.

ON Fixation, Sectioning, Paraphenylenediamine (PPD) Staining, and Scoring

ONs were processed for PPD staining as previously described [38]. Sections were imaged on a Zeiss Axioimager Z2 upright microscope using a ×40 magnification oil objective. Images were scored using a semi-quantitative three-score system where each nerve was assigned a score of no or early (NOE), moderate (MOD), or severe (SEV) glaucoma [20]. All ONs were scored by two masked observers. The statistical significance between the distributions of different groups was calculated using $\chi^2$ test.

Results:

mCherry-BCLX$_L$, Prevents GFP-BAX Recruitment In Vitro

Figure 1:
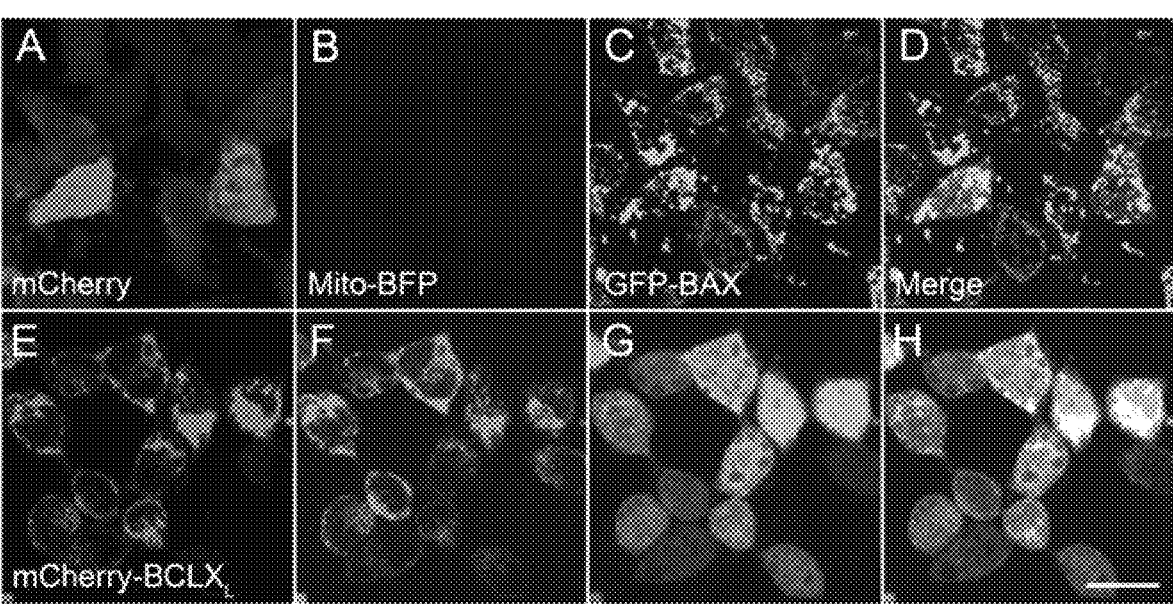
FIG. 1 demonstrates that mCherry-BCLX$_L$ colocalizes with the mitochondria and prevents BAX recruitment in vitro. Representative images of D407 cells expressing mCherry (A-D), mCherry-BCLX$_L$ (E-H) along with mito-BFP (B and F) and GFP-BAX (C and G) 3.5 h after treatment with 1 μM staurosporine (STS). Note that mito-BFP fluorescence is rapidly lost when the mitochondrial outer membrane becomes permeabilized and the mitochondria become fragmented, which is why B has dramatically reduced fluorescence. Scale bar=10 μm. Live cell imaging was used to track the localization of GFP-BAX for 3.5 h after STS treatment. The percentage of cells in each condition with punctate localization is quantified in I. N=163 and 146 cells for the mCherry and mCherry-BCLX$_L$ expressing groups, respectively. $\chi^2$ test was used to assess the significance of the difference in percentage between each group at each time point. P<0.0005 at 30 min, P<0.00001 at 120 min, and P<0.00001 at 210 min.
Figure 1:
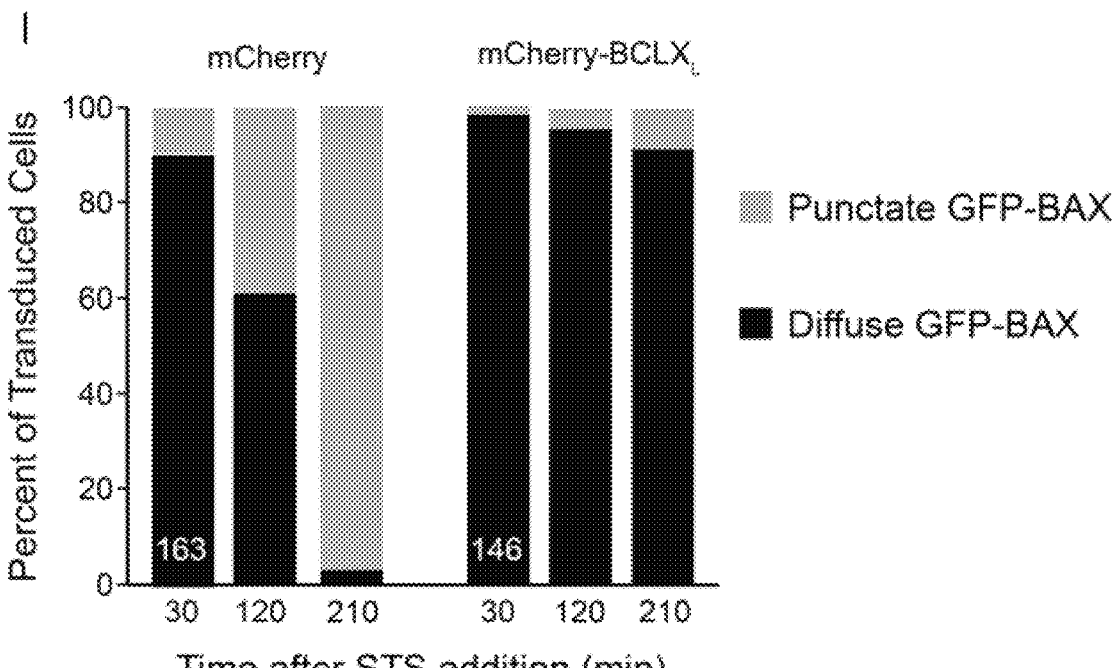

The canonical function of mCherry-BCLX$_L$, i.e., preventing BAX from accumulating on the mitochondria, was verified in vitro. As expected, mCherry-BCLX$_L$ colocalized with a mitochondrially localized BFP (FIG. 1E, F, H). The ability of mCherry-BCLX$_L$ to prevent GFP-BAX translocation was assessed in cells after STS treatment. Over 95% of cells expressing mCherry and GFP-BAX exhibited GFP-BAX translocation to mitochondria within 3.5 h (FIG. 1A-D, I). Conversely, only 8% of cells expressing mCherry-BCLX$_L$ and GFP-BAX exhibited punctate GFP-BAX (FIG. 1E-I).

AAV2-Pgk-mCherry-BclX$_L$, Efficiently Transduces RGCs

Figure 2:
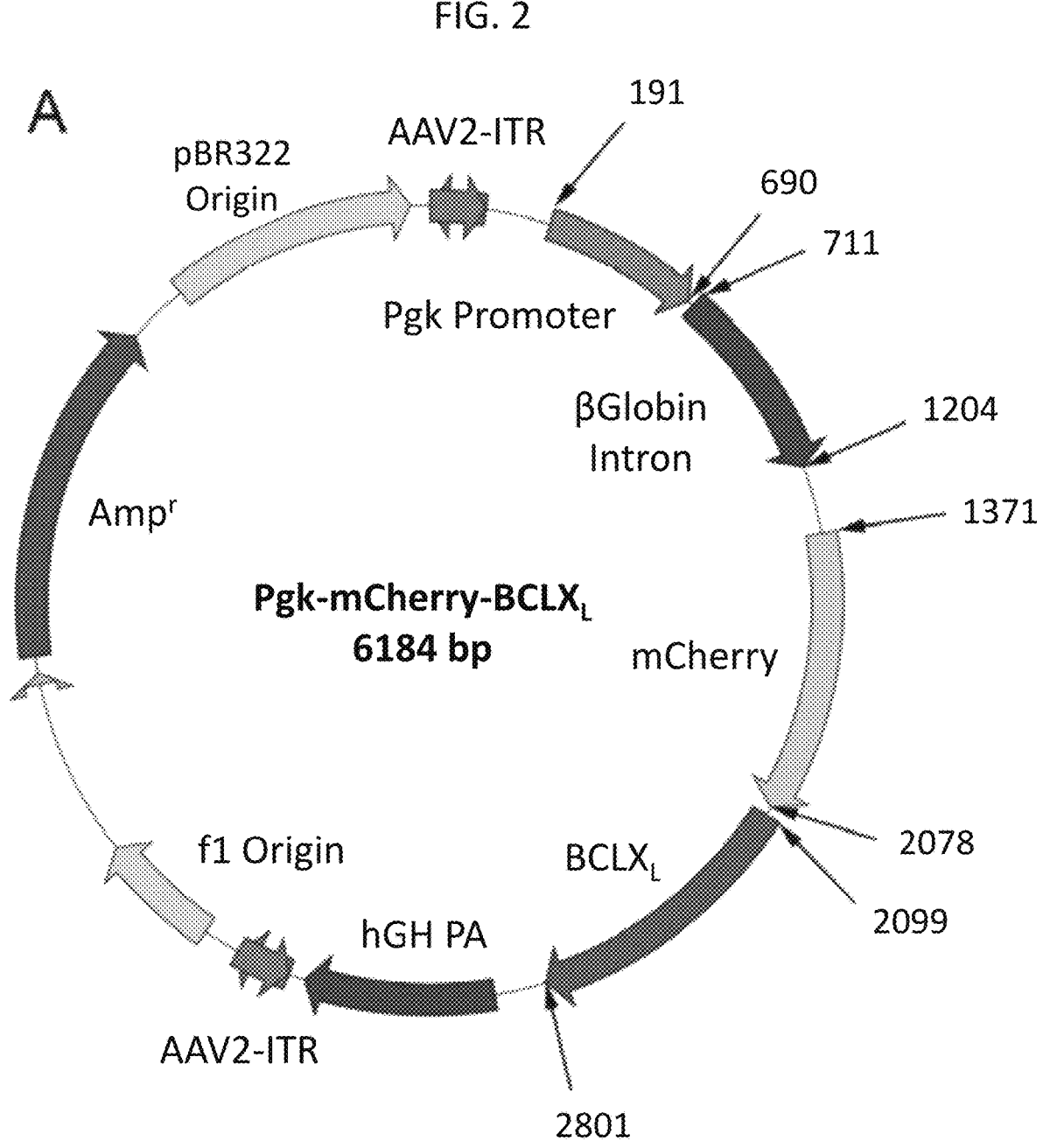
FIG. 2 shows the intraretinal expression pattern of mCherry-BCLX$_L$ following AAV2-Pgk-mCherry-BclX$_L$, transduction. A: A map showing the plasmid that was packaged into AAV2-Pgk-mCherry-BclX$_L$. B: A retinal whole-mount preparation, 4 weeks after intravitreal injection, showing widespread expression of the transgene across the retina. Scale bar=450 μm. C-F: Co-localization of BRN3A-positive cells that were transduced by AAV2-Pgk-mCherry-BclX$_L$, (arrows). An asterisk labels a transgene expressing cell that is BRN3A negative but appears to project a labeled axon into the nerve fiber layer. Only the ganglion cell layer (GCL) is shown. Scale bar=20 μm. G: Graph showing the percentages of total cells in the GCL and BRN3A-positive cells that expressed the mCherry-BCLX$_L$ transgene (mean±standard deviation).
Figure 2:
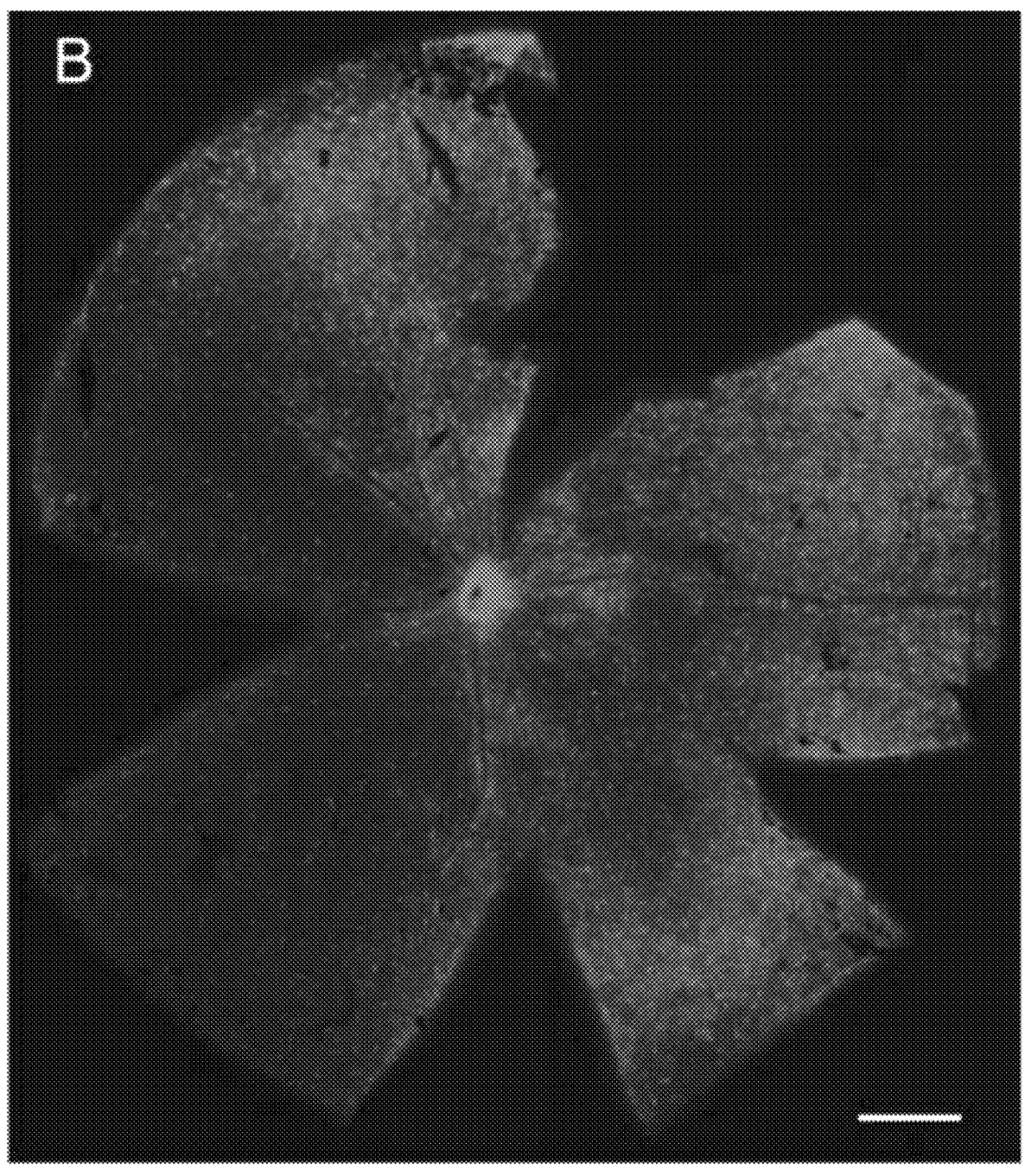
Figure 2:
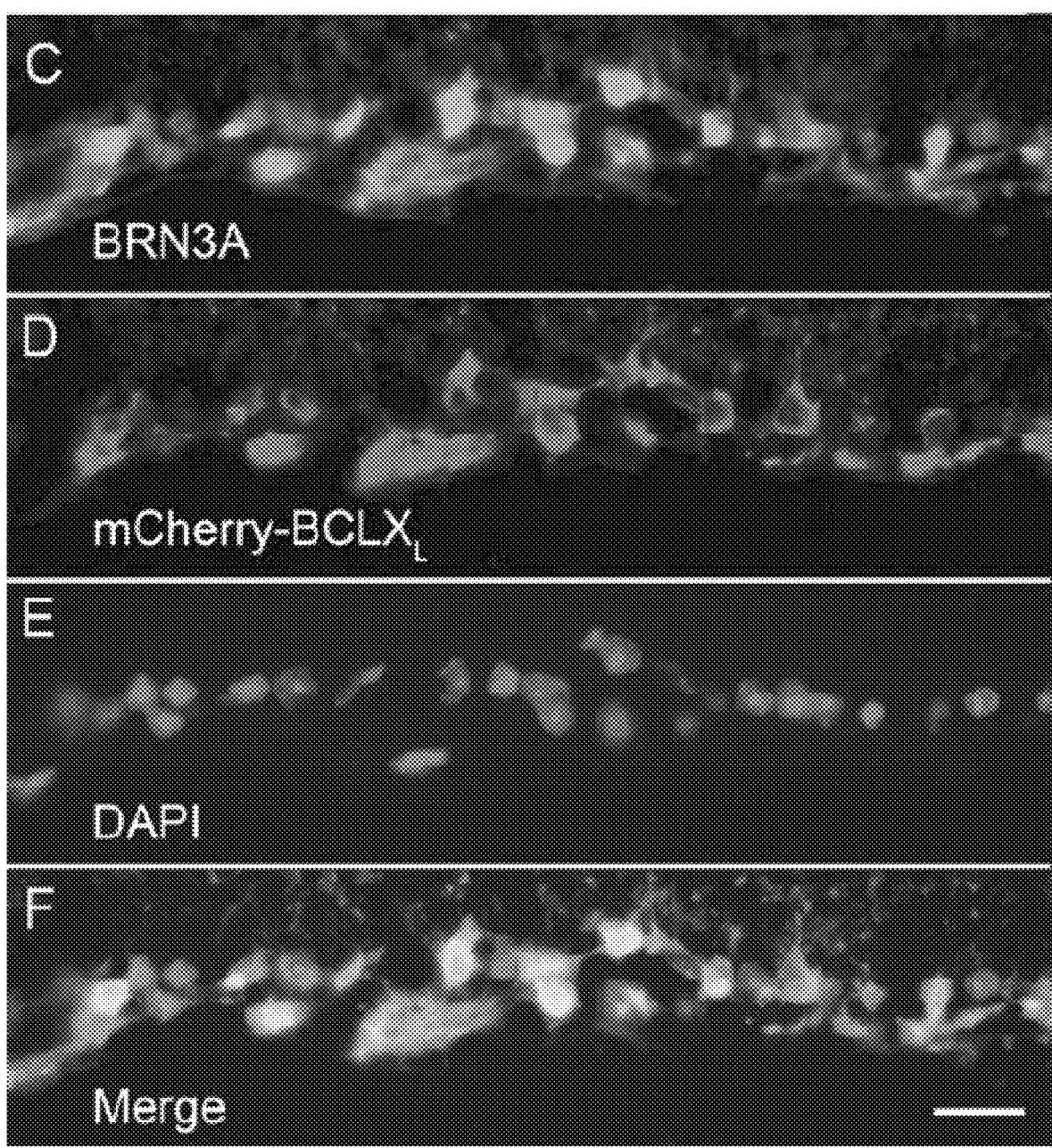
Figure 2:
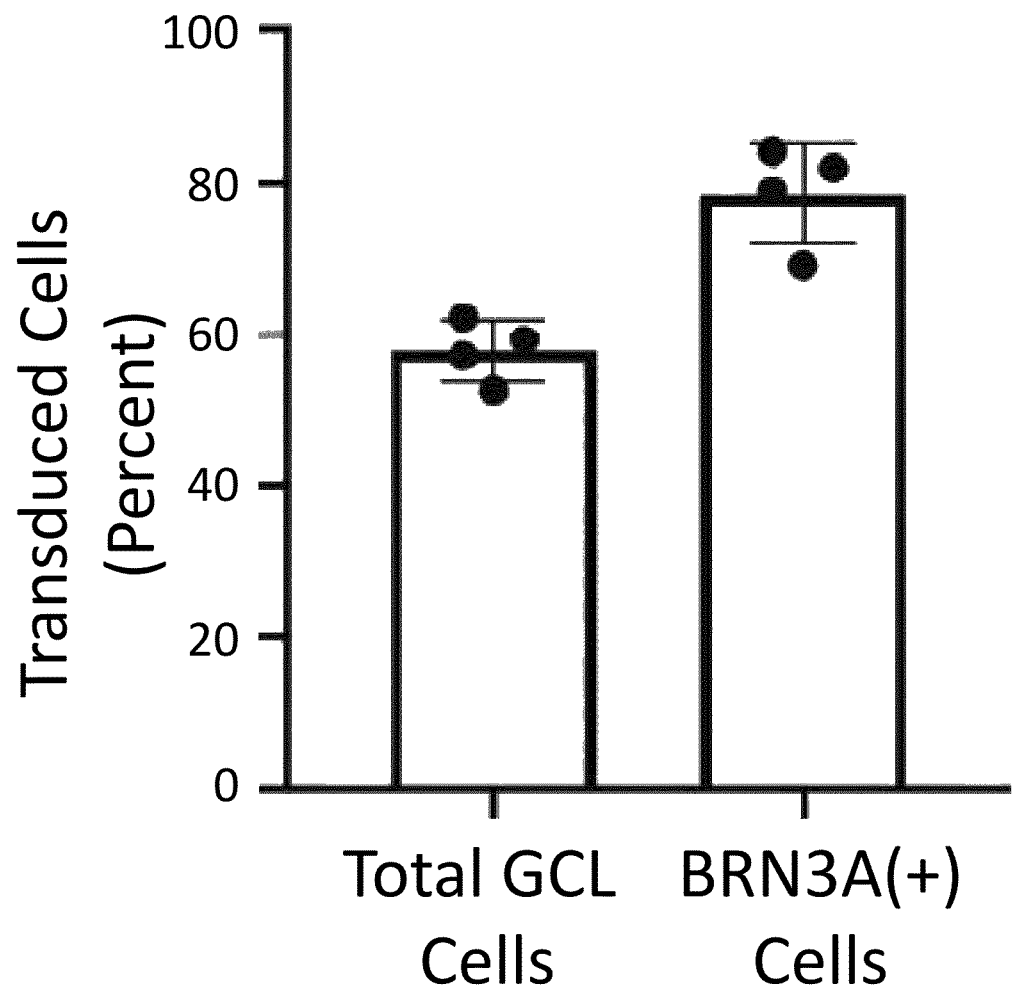

Next, the transduction efficiency of AAV2-Pgk-mCherry-BclX$_L$, (FIG. 2A) was measured. Evaluation of retinal whole mounts 4 weeks after intravitreal injection showed widespread expression of the transgene in the ganglion cell layer (FIG. 2B). Histologic examination of transduced retinas showed that AAV2-Pgk-mCherry-BclX$_L$, transduced over 50% of the cells in the ganglion cell layer of the retina, which is consistent with the percentage of RGCs in this layer [39]. Colocalization with the RGC marker BRN3A demonstrated that nearly 80% of BRN3A+ cells were transduced (FIG. 2C-G). AAV2 also transduces other retinal cell types [31]. We observed transduction of both horizontal and amacrine cells based on colocalization with an antibody to Calbindin (FIG. 9).

Figure 3:
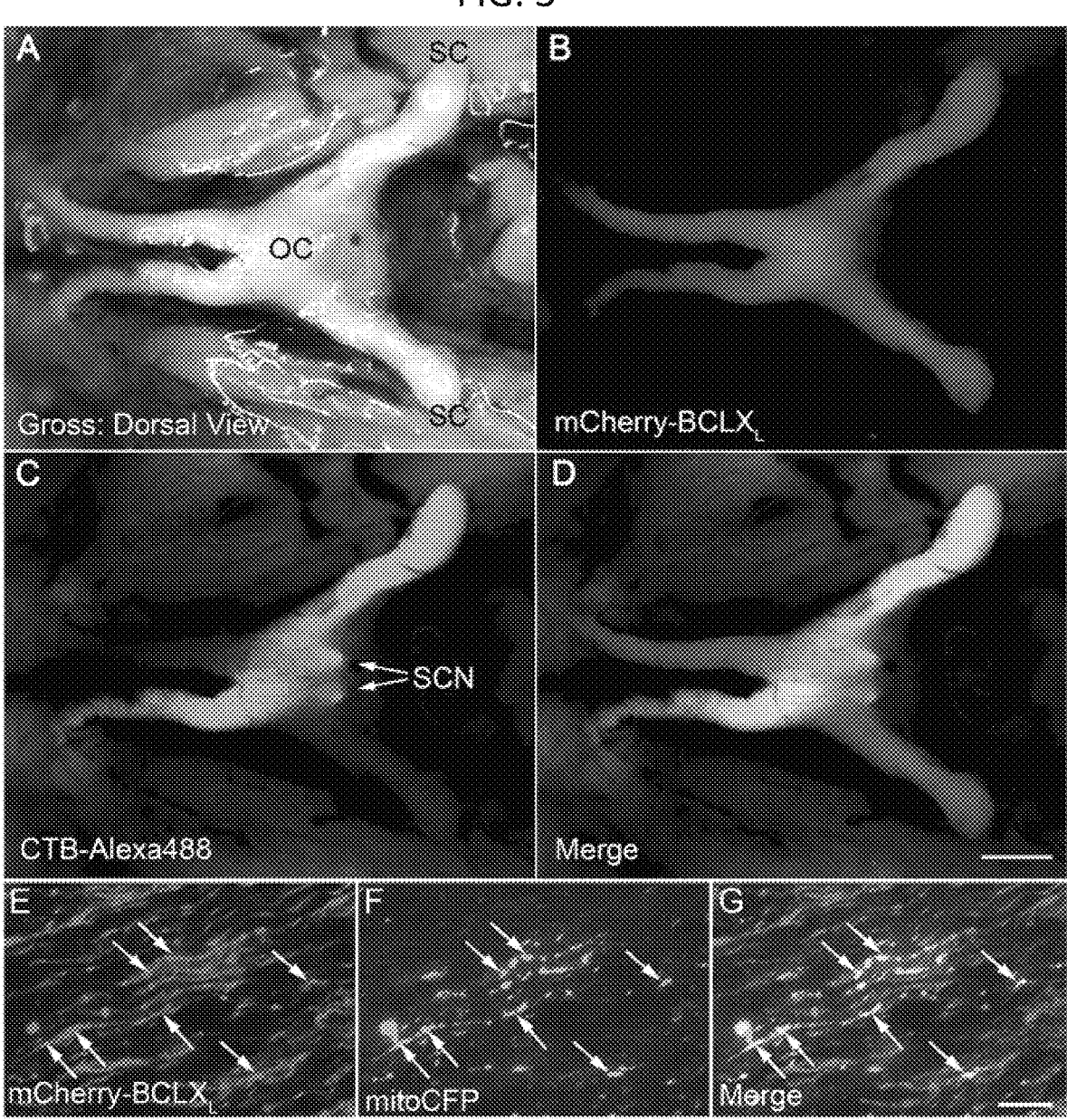
FIG. 3 demonstrates that mCherry-BCLX$_L$ is robustly expressed in the RGC axons in the optic nerve. A: A brightfield image of the dorsal view of the optic nerves from a mouse transduced bilaterally with AAV2-Pgk-mCherry-BclX$_L$, and later injected unilaterally (left eye only) with CTB-Alexa488. B: The same field imaged for mCherry-BCLX$_L$ fluorescence. The fusion protein can be seen in the optic nerve distal to the optic chiasm (OC) and approaching the superior colliculus (SC). C: The same field imaged for CTB-Alexa488 fluorescence. Arrows denote fluorescence in the suprachiasmatic nucleus (SCN). D: A merged image of B, C showing bilateral mCherry-BCLX$_L$ expression and unilateral CTB-488. Scale bar=1 mm. E-G: Histologic sections of the optic nerve from a transduced eye of a transgenic mouse expressing Thy1-mitoCFP to label RGC mitochondria. Note that not all RGCs express Thy1-mitoCFP in this line. The mCherry-BCLX$_L$ transgene is present throughout individual axons but concentrated in regions that correspond to axonal mitochondria (arrows). Scale bar=5 μm.

The mCherry-BCLX$_L$ fusion protein was also observed throughout the optic tract of transduced eyes, demonstrating its presence in RGC axons (FIG. 3). Unilateral injection of CTB-488, to label axons, in a mouse that was bilaterally injected with AAV2-Pgk-mCherry-BclX$_L$ showed colocalization with the fusion protein, confirming axonal labeling. CTB-488 also showed bilateral fluorescence in the suprachiasmatic nucleus (SCN; FIG. 3C arrows), the only region of the rodent brain that is innervated equally on the ipsilateral and contralateral sides by projections from one ON [41], principally from intrinsically photosensitive RGCs [42]. No mCherry-BCLX$_L$ fluorescence was detected in the SCN, suggesting that AAV2-Pgk-mCherry-BclX$_L$, did not transduce this population of RGCs. Transgenic mice expressing Thy1-mitoCFP to label RGC mitochondria were also injected. ON sections showed colocalization of mCherry-BCLX$_L$ and mitochondria in RGC axons (FIG. 3E-G).

mCherry-BCLX$_L$, Prevents Cell Loss in RGC Layer Following ONC

Figure 4:
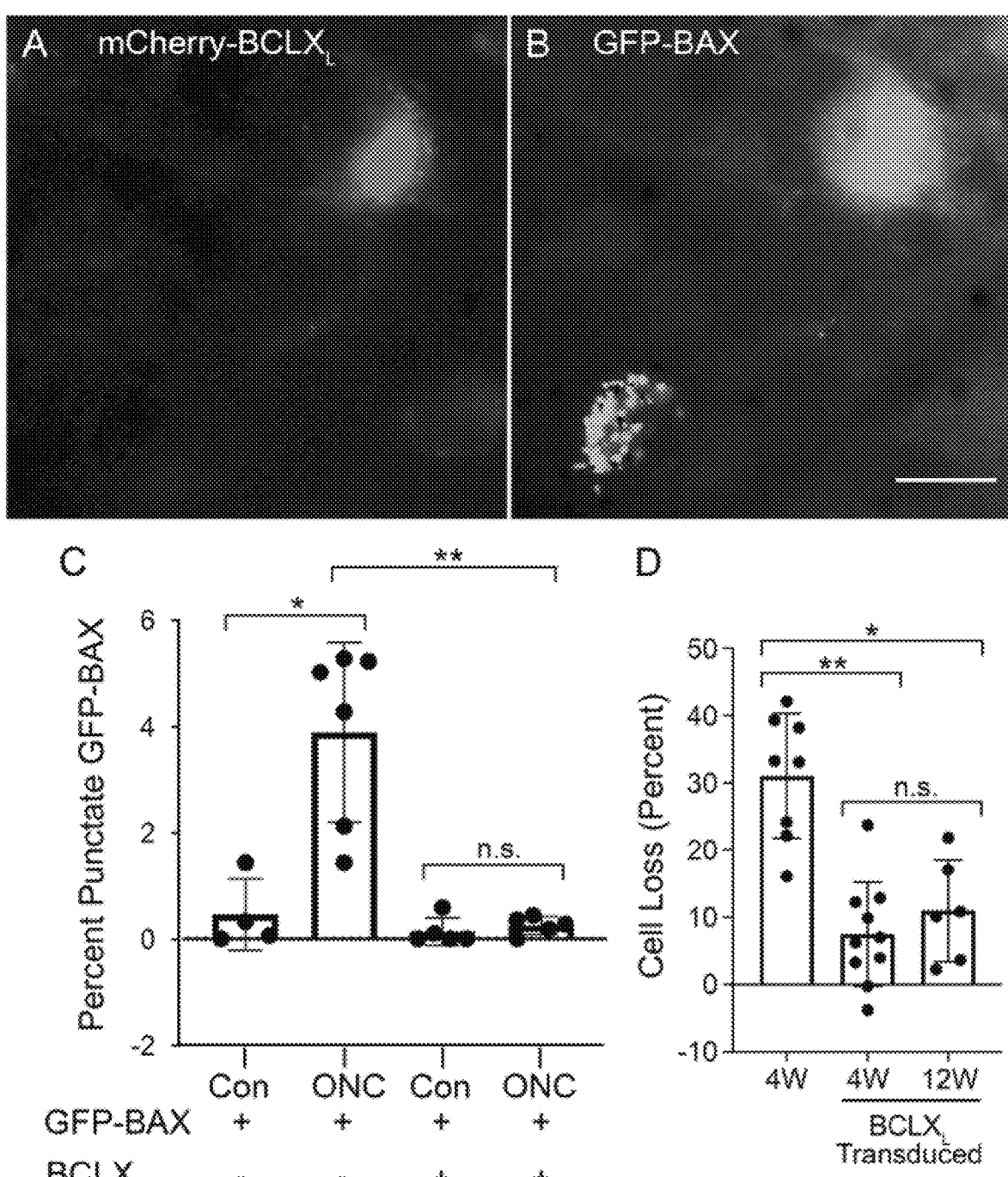
FIG. 4 demonstrates that mCherry-BCLX$_L$ expression prevents BAX translocation and attenuates cell loss after optic nerve crush. A, B: Panels showing mCherry-BCLX$_L$ and GFP-BAX expression, respectively, in a retinal whole mount from a mouse that had undergone ONC to induce BAX activation. The cell expressing mCherry-BCLX$_L$ shows diffuse localization of GFP-BAX and the cell that is not expressing mCherry-BCLX$_L$ has punctate, translocated GFP-BAX. Scale bar=10 μm. C: A quantification of the phenomenon displayed in A, B. In this experiment, all mice were transduced with AAV2-Pgk-GFP-BAX Half the mice also received an injection of AAV2-Pgk-mCherry-BCLX$_L$. The percentage of GFP-BAX-labeled cells with punctate GFP-BAX was quantified 1 week after ONC in untransduced mice and mice that had been bilaterally transduced with AAV2-Pgk-mCherry-BclX$_L$ 1 month before ONC (mean±standard deviation). Significance was determined using a one-sided t test. In all, 4-7 mice were used per group.

We tested the ability of the BCLX$_L$ fusion protein to protect RGCs from apoptosis following acute optic nerve damage in mice subjected to optic nerve crush (ONC) as a proof-of-principal test (FIG. 4). Mice were co-transduced with AAV2s expressing mCherry-BCLX$_L$ or GFP-BAX. Prevention of BAX translocation after ONC was assessed by counting the percentage of cells with punctate GFP-BAX in the presence or absence of mCherry-BCLX$_L$ (FIG. 4A, B). One week after ONC, mCherry-BCLX$_L$ overexpression prevented a significant change in the percentage of cells with punctate GFP-BAX (FIG. 4C).

Next, we tested the ability of mCherry-BCLX$_L$ to provide sustained protection to RGCs by examining the pattern of cell loss in the RGC layer after ONC. Both 4 and 12 weeks post-ONC, AAV2-Pgk-mCherry-BclX$_L$, transduced retinas had significantly less cell loss than untransduced retinas analyzed 4 weeks post-ONC (FIG. 4D).

AAV2 Transduction does not Prevent IOP Elevation in DBA/2J Mice

Next, we examined whether AAV2-Pgk-mCherry-BclX$_L$, affected the progression of ocular hypertension in DBA/2J mice. DBA/2J mice carry mutations in two genes, Gpnmb and Tyrp1, that are associated with melanocyte biosynthesis. At a young age, DBA/2J mice exhibit no outward characteristics of glaucomatous disease. At 6-8 months of age, however, they show signs of iris stromal atrophy and pigment dispersion, defects which are linked to the genetic mutations that they carry. These changes in the anterior chamber lead to pathology of the aqueous humor outflow channels, including pigment clogging of the trabecular meshwork, and closure of the angle due to synechia formation between the cornea and iris. As a result of the compromise of the outflow of aqueous humor, the IOP rises in these mice beginning around the ages of 7-8 months. In general, the IOP elevation is moderate, with pressures reaching into the high 20's to low 30's mmHg. Ocular hypertension is sustained in eyes to ages of 12-13 months after which it declines to normal levels. The reason for the decline is not known, but it may be related to late pathology of the ciliary body causing a decrease in aqueous production. Ocular hypertension in the DBA/2J mouse leads to glaucoma, including the degeneration of the optic nerve and the loss of RGCs from the retina. Although this is an inbred strain, IOP elevation and glaucomatous pathology is not synchronous or necessarily bilateral in any given aging mouse. As a consequence, study design with this model requires large cohorts of animals for each treatment group, and each eye of every mouse is treated as an independent data point in the study. The industry standard for glaucoma studies involving these mice is to assess glaucomatous pathology at 10.5 months of age, when approximately 50-60% of the optic nerves within a cohort of mice has reached near end-stage glaucomatous damage.

Histological examination of transduced cells in the conventional aqueous outflow pathway showed that mCherry-$BCLX_L$ was expressed in the non-pigmented epithelial cells of the ciliary body but not in cells of the trabecular meshwork or Schlemm's canal (FIG. 5A-D). Longitudinal measurements of IOP in AAV2-Pgk-mCherry-BclX$_L$ transduced mice, compared to untransduced mice, revealed four individual timepoints with statistically significant differences in IOP between groups (FIG. 5E). Regression modeling failed to detect a difference between the trends of the groups over the entire course of the experiment, indicating that mCherry-$BCLX_L$ did not significantly impact longitudinal IOP elevation.

mCherry-$BCLX_L$, Prevents RGC Degeneration in Aged DBA/2J Mice

Next, we tested whether mCherry-$BCLX_L$ would prevent RGC degeneration in aged DBA/2J mice. Retinal whole mounts showed robust expression of the transgene in transduced retinas at both 10.5 and 12 months of age (FIG. 10). The protective effect of mCherry-$BCLX_L$ was first measured by quantifying changes in the abundance of transcripts selectively expressed in RGCs using qPCR. At 10.5 months of age, $BCLX_L$ treated retinas exhibited a nearly 5-fold increase in BclX$_L$ transcript abundance (FIG. 6A). These retinas also had significantly higher abundances of the RGC-selective mRNAs Nefl, Nrn1, Thy1, Sncg, and Tubb3 transcripts than untreated retinas, which showed a nearly uniform decrease in these mRNAs (FIG. 6B-F), indicating that $BCLX_L$ treatment preserved RGC-specific gene expression. Both naive and treated retinas exhibited similar increases in Gfap and Hsp27 transcript abundance relative to young mice, indicating that $BCLX_L$ treatment did not prevent retinal stress (FIG. 6G, H). Interestingly, treated retinas expressed more Gap43 (FIG. 6I), a marker of axon regeneration [43].

$BCLX_L$ gene therapy prevented glaucomatous degeneration. $BCLX_L$-treated mice had significantly fewer moderately and severely degenerated ONs compared to naive animals at 10.5 months of age (FIG. 7). $BCLX_L$ gene therapy was profoundly protective of axons in the ONs of 12-month-old animals, an age when Bax deficiency was not protective [6]. In fact, the distribution of ON scores for 12-month-old $BCLX_L$-treated mice showed modestly, but significantly, less degeneration than the distribution of scores for 10.5-month-old $BCLX_L$-treated mice. Stratification of data where we had both cell density counts and ON scores for the same eye showed that there was an association with reduced cell density and SEV ON score, while eyes exhibiting MOD ON damage typically showed no significant loss of cell density compared to eyes with NOE damage within a given cohort (FIG. 8). We interpret the presence of SEV damage and cell loss in some mice from treated cohorts as a consequence of less-than-optimal viral transduction, although other factors such as extreme ocular hypertension cannot be ruled out. Additionally, cell density in retinas from eyes with NOE ON damage, in most cohorts of aged mice, still exhibited an overall 10% decline in total cell density when compared with young mice, suggesting age-related effects not affected by the gene therapy.

These data reflect the protective effect of $BCLX_L$ therapy if applied prophylactically (4-5 months). To test whether we can achieve similar protection during the period of first onset of elevated IOP, mice were transduced at 7 months and aged to 10.5 months. These mice exhibited a similar level of protection compared to mice transduced at an earlier age (FIG. 11).

mCherry-$BCLX_L$, Protects Visual Function in Aged DBA/2J Mice

To assess the function of the optic nerve and RGCs in transduced mice, we conducted visual evoked potential (VEP), scotopic flash electroretinogram (ERG), and pattern ERG (pERG) testing on small cohorts of aged DBA/2J mice (N=7-10 mice per cohort) that had received injections of AAV2-Pgk-mCherry or AAV2-Pgk-mCherry-$BCLX_L$ viruses at 2.5 months of age and compared them with naïve mice when they reached 10.5 months of age. ERG is used to assess outer retinal function (rod and cone photoreceptors and secondary neurons in the inner nuclear layer), whereas pERG is used in combination with VEP to assess inner retinal function, principally RGCs.

All animals exhibited normal ERG responses within the physiological levels of light flashes (<10 cd·s/m2), but AAV2-Pgk-mCherry-$BCLX_L$ treated mice exhibited a decline in their response at extremely high light flash intensity (FIG. 12A-C), suggesting that the mCherry-$BCLX_L$ transgene moderately suppresses outer retinal function. At the highest flash intensity (25 cd·s/m2), there was a significant suppression of the c-wave amplitude with the mCherry-$BCLX_L$ transgene, indicating a potential negative effect on the retinal pigmented epithelium (FIG. 12C).

Assessment of RGC function using VEP and pERG showed that AAV2-Pgk-mCherry-$BCLX_L$ treated mice exhibited a significant preservation of visual function compared to both age-matched naïve and AAV2-Pgk-mCherry treated mice (FIG. 12D), suggesting that the mCherry-$BCLX_L$ transgene provided a significant protective effect to RGC function in glaucomatous mice. This was apparent when comparing mCherry-$BCLX_L$ to mCherry transduced mice in the VEP measurement (*P=0.035) and to both mCherry and naïve mice in the pERG measurement (*P<0.05).

Discussion:

The mCherry-$BCLX_L$ fusion protein prevented BAX translocation both in vitro and in vivo (in RGCs) after exposure to acute apoptotic stimuli. In the DBA/2J mouse model of glaucoma, mCherry-$BCLX_L$ conferred extended protection to the retina and the ON that exceeded the reported protective effect of genetic deletion of Bax. Therefore, $BCLX_L$ must protect RGCs through more than simple inhibition of BAX.

There are several potential explanations for the additional protection conferred by mCherry-$BCLX_L$. Recent literature has focused on the axodegenerative pathway catalyzed by SARM1 [5, 44, 45]. A combination of the Wld$^s$ allele, which prevents SARM1 activation, and depletion of BAX, via genetic deletion of one Bax allele, appeared to provide a greater protective effect to ONs of DBA/2J mice than either treatment alone [3]. Our results suggest that $BCLX_L$ inhibits both the BAX and SARM1 pathways. SARM1 activation is the result of an increased ratio of nicotinamide mononucle-otide (NMN) to NAD$^+$ [46]. Future studies should examine whether BCLX$_L$ stabilizes the ratio of NMN:NAD$^+$ or acts by some indirect mechanism, such as increasing the resil-iency of the mitochondria, consistent with growing evidence that an age-related decline in mitochondrial performance is a contributing factor to glaucomatous neurodegeneration [25, 47]. Interestingly, BCLX$_L$ has been shown to improve the metabolic efficiency of mitochondria and increase over-all mitochondrial biomass [48-50]. Future studies should explore how BCLX$_L$ augments mitochondrial function in RGCs.

A final possibility is that BCLX$_L$ helps the RGC maintain axonal transport. Axonal transport disruption is one of the earliest events in glaucoma [51]. The sustained protection in glaucomatous animals by our fusion protein suggests that mCherry-BCLX$_L$ was present in axons at high enough concentrations throughout the course of the disease to coun-teract degenerative signaling. A by-product of putative aug-mentation of mitochondrial physiology by BCLX$_L$ may be uninterrupted axonal transport.

BCLX$_L$ gene therapy yielded better preservation of ONs in 12-month-old DBA/2J mice than in 10.5-month-old mice. Since the 10.5- and 12-month groups were performed sequentially, this variation may be the result of a stochastic batch effect. However, the increased abundance of RGC-specific transcripts and the regeneration marker Gap43 sug-gests some level of spontaneous regeneration occurring in these mice after ocular hypertension subsides, a process which begins between 11 and 12 months of age in these mice [20]. The effect of BCLX$_L$ on the regenerative potential of RGCs is a promising, untested future direction.

These results suggest that BCLX$_L$ gene therapy preserves RGC anatomy and gene expression in a mouse model of glaucoma. To build on these findings, future studies should test BCLX$_L$ gene therapy in a larger animal model of glaucoma. Larger animals more accurately reflect the human anatomy and disease and the potential challenges with gene therapy in human retinas [52]. Additionally, our experiments did not examine the potential to preserve RGC function, which should be a priority in a model system better suited to clinical examination. Translational application of BCLX$_L$ gene therapy will also require evaluating the safety issues associated with long-term expression of this anti-apoptotic protein, including its possible effects on tumorigenesis [53, 54] and increased susceptibility to viral infections [55]. Future Studies:

A pilot study will be performed to optimize viral trans-duction of cat RGCs using AAV2/2-mediated gene transfer in large animals. Cats from an outbred colony of cats that develop chronic inherited congenital glaucoma will be used. The cats will allow for efficacy testing of the same clinical platforms used on humans. Studies in cats represent a potential technical hurdle, however, since there have only a few attempts at using gene therapy to successfully transduce cells of the feline retina. Thus, this pilot study will examine and perfect methods for efficiently transducing the cat retina using an intravitreal injection.

Efficacy studies of AAV2/2-Pgk-(mCherry)-BCLX$_L$ in cat and dog models of glaucoma will be conducted as well. Once gene delivery protocols for the cat retina have been established, the efficacy studies in the glaucoma model will be initiated. This part of the pre-clinical investigation is expected to yield unambiguous data regarding the ability of the BCLX$_L$ gene therapy to prevent glaucomatous neurode-generation and loss of RGC function. Initial studies are expected to be conducted in the cat model of inherited glaucoma. Studies using acute ocular hypertension in dogs will be completed using a self-complementary AAV con-struct of the therapeutic transgene (see below).

A self-complementary AAV (scAAV) vector would enable more rapid and more efficient transgene expression in RGCs, which normally take up to 1 month to replicate the single stranded viral genome after transduction. The scAAV con-struct would require removal of the mCherry reporter region, and likely removal of the R Globin second intron, which currently lies upstream of the translation start site.

REFERENCES

1. Quigley H A. Glaucoma. *Lancet.* 2011; 377:1367-77. doi: 10.1016/S0140-6736(10)61423-7.
2. Leske M C, Heijl A, Hussein M, Bengtsson B, Hyman L, Komaroff E, et al. Factors for glaucoma progression and the effect of treatment: the early manifest glaucoma trial. *Arch Ophthalmol.* 2003; 121:48-56. doi: 10.1001/ar-chopht.121.1.48.
3. Howell G R, Libby R T, Jakobs T C, Smith R S, Phalan F C, Barter J W, et al. Axons of retinal ganglion cells are insulted in the optic nerve early in DBA/2J glaucoma. *J Cell Biol.* 2007; 179:1523-37. doi: 10.1083/jcb.200706181.
4. Osterloh J M, Yang J, Rooney T M, Fox A N, Adalbert R, Powell E H, et al. dSarm/Sarm1 is required for activation of an injury-induced axon death pathway. *Science.* 2012; 337:481-4. doi: 10.1126/science.1223899.
5. Fernandes K A, Mitchell K L, Patel A, Marola O J, Shrager P, Zack D J, et al. Role of SARM1 and DR6 in retinal ganglion cell axonal and somal degeneration fol-lowing axonal injury. *Exp Eye Res.* 2018; 171:54-61. doi: 10.1016/j.exer.2018.03.007.
6. Libby R T, Li Y, Savinova O V, Barter J, Smith R S, Nickells R W, et al. Susceptibility to neurodegeneration in a glaucoma Is modified by Bax gene dosage. PLoS Genet. 2005. 10.1371/journal.pgen.0010004.
7. Nikolaev A, McLaughlin T, O'Leary D D M, Tessier-Lavigne M. APP binds DR6 to trigger axon pruning and neuron death via distinct caspases. *Nature.* 2009; 457: 981-9. doi: 10.1038/nature07767.
8. Simon D J, Weimer R M, Mclaughlin T, Kallop D, Stanger K, Yang J, et al. A caspase cascade regulating develop-mental axon degeneration. *J Neurosci.* 2012; 32:17540-53. doi: 10.1523/JNEUROSCI.3012-12.2012.
9. Simon D J, Pitts J, Hertz N T, Tesic Mark M, Molina H, Tessier M, et al. Axon degeneration gated by retrograde activation of somatic pro-apoptotic signaling. *Cell.* 2016; 164:1031-45. doi: 10.1016/j.cell.2016.01.032.
10. Li Y, Schlamp C L, Poulsen K P, Nickells R W. Bax-dependent and independent pathways of retinal gan-glion cell death induced by different damaging stimuli. *Exp Eye Res.* 2000; 71:209-13. doi: 10.1006/exer.2000.0873.
11. Sun Y F, Yu L Y, Saarma M, Timmusk T, Arumae U. Neuron-specific Bcl-2 homology 3 domain-only splice variant of Bak is anti-apoptotic in neurons, but pro-apoptotic in non-neuronal cells. *J Biol Chem.* 2001; 276:16240-7. doi: 10.1074/jbc.M010419200.
12. Levin L A, Schlamp C L, Spieldoch R L, Geszvain K M, Nickells R W. Identification of the bcl-2 family of genes in the rat retina. *Investig Ophthalmol Vis Sci.* 1997; 38:2545-53.
13. Edlich F, Banerjee S, Suzuki M, Cleland M M, Arnoult D, Wang C, et al. Bcl-xL retrotranslocates Bax from the mitochondria into the cytosol. *Cell.* 2011; 145:104-16. doi: 10.1016/j.cell.2011.02.034.

14. Gonzalez-Garcia M, Garcia I, Ding L, O'Shea S, Boise L H, Thompson C B, et al. bcl-x is expressed in embryonic and postnatal neural tissues and functions to prevent neuronal cell death. *Proc Natl Acad Sci USA.* 1995; 92:4304-8. doi: 10.1073/pnas.92.10.4304.

15. Parsadanian A S, Cheng Y, Keller-Peck C R, Holtzman D M, Snider W D. Bcl-x(L) is an antiapoptotic regulator for postnatal CNS neurons. *J Neurosci.* 1998; 18:1009-19. doi: 10.1523/JNEUROSCI.18-03-01009.1998.

16. Yin W, Cao G, Johnnides M J, Signore A P, Luo Y, Hickey R W, et al. TAT-mediated delivery of Bcl-xL protein is neuroprotective against neonatal hypoxic-ischemic brain injury via inhibition of caspases and AIF. *Neurobiol Dis.* 2006; 21:358-71. doi: 10.1016/j.nbd.2005.07.015.

17. Liu X H, Collier R J, Youle R J. Inhibition of axotomy-induced neuronal apoptosis by extracellular delivery of a Bcl-X L fusion protein. *J Biol Chem.* 2001; 276:46326-32. doi: 10.1074/jbc.M108930200.

18. Malik J M I, Shevtsova Z, Bahr M, Kügler S, Shevstova Z, Bahr M, et al. Long-term in vivo inhibition of CNS neurodegeneration by Bcl-X L gene transfer. *Mol Ther.* 2005; 11:373-81. doi: 10.1016/j.ymthe.2004.11.014.

19. John S W M, Smith R S, Savinova O V, Hawes N L, Chang B, Turnbull D, et al. Essential iris atrophy, pigment dispersion, and glaucoma in DBA/2J mice. *Investig Ophthalmol Vis Sci.* 1998; 39:951-62.

20. Libby R T, Anderson M G, Pang I-H, Robinson Z H, Savinova O V, Cosma I M, et al. Inherited glaucoma in DBA/2J mice: pertinent disease features for studying the neurodegeneration. *Vis Neurosci.* 2005; 22:637-48. doi: 10.1017/S0952523805225130.

21. Schlamp C L, Li Y, Dietz J A, Janssen K T, Nickells R W. Progressive ganglion cell loss and optic nerve degeneration in DBA/2J mice is variable and asymmetric. *BMC Neurosci.* 2006; 7:1-14. doi: 10.1186/1471-2202-7-66.

22. Harder J M, Williams P A, Braine C, Yang H, Thomas J, Foxworth N, et al. Anaphylatoxin receptor C3AR1 promotes optic nerve degeneration in DBA/2J mice. *J Neuroinflammation.* 2020. 10.21203/rs.3.rs-39367/v1.

23. Howell G R, Macalinao D G, Sousa G L, Walden M, Soto I, Kneeland S C, et al. Molecular clustering identifies complement and endothelin induction as early events in a mouse model of glaucoma. *J Clin Investig.* 2011; 121: 1429-44. doi: 10.1172/JCI44646.

24. Harder J M, Fernandes K A, Libby R T. The Bcl-2 family member BIM has multiple glaucoma-relevant functions in DBA/2J mice. *Sci Rep.* 2012; 2:530. doi: 10.1038/srep00530.

25. Williams P A, Harder J M, Foxworth N E, Cochran K E, Philip V M, Porciatti V, et al. Vitamin B3 modulates mitochondrial vulnerability and prevents glaucoma in aged mice. *Science.* 2017; 355:756-60. doi: 10.1126/science.aal0092.

26. Weng C Y. Bilateral subretinal Voretigene Neparvovec-rzyl (Luxturna) *Gene Ther Ophthalmol* Retina. 2019; 3:450. doi: 10.1016/j.oret.2019.02.007.

27. Wang D, Tai P W L, Gao G. Adeno-associated virus vector as a platform for gene therapy delivery. *Nat Rev Drug Discov.* 2019; 18:358-78. doi: 10.1038/s41573-019-0012-9.

28. Martin K R G, Quigley H A, Zack D J, Levkovitch-Verbin H, Kielczewski J, Valenta D, et al. Gene therapy with brain-derived neurotrophic factor as a protection:

retinal ganglion cells in a rat glaucoma model. *Investig Opthalmol Vis Sci.* 2003; 44:4357-65. doi: 10.1167/iovs.02-1332.

29. Mosinger Ogilvie J, Deckwerth T L, Knudson C M, Korsmeyer S J. Supression of developmental retinal cell death but not of photoreceptor degeneration in Bax-deficient mice. *Invest Ophthalmol Vis Sci.* 1998; 39:1713-20.

30. Donahue R J, Maes M E, Grosser J A, Nickells R W. BAX-depleted retinal ganglion cells survive and become quiescent following optic nerve damage. *Mol Neurobiol.* 2020; 57:1070-84. doi: 10.1007/s12035-019-01783-7.

31. Nickells R W, Schmitt H M, Maes M E, Schlamp C L. AAV2-mediated transduction of the mouse retina after optic nerve injury. *Investig Opthalmol Vis Sci.* 2017; 58:6091. doi: 10.1167/iovs.17-22634.

32. Semaan S J, Nickells R W. The apoptotic response in HCT116 cancer cells becomes rapidly saturated with increasing expression of a GFP-BAX fusion protein. *BMC Cancer.* 2010; 10:554.

33. Maes M E, Schlamp C L, Nickells R W. Live-cell imaging to measure BAX recruitment kinetics to mito-chondria during apoptosis. *PLoS ONE.* 2017; 12:e0184434.

34. Li Y, Schlamp C L, Nickells R W. Experimental induction of retinal ganglion cell death in adult mice. Investig *Ophthalmol Vis Sci.* 1999; 40:1004-8.

35. Schmitt H M, Grosser J A, Schlamp C L, Nickells R W. Targeting HDAC3 in the DBA/2J spontaneous mouse model of glaucoma. *Exp Eye Res.* 2020; 200:108244. doi: 10.1016/j.exer.2020.108244.

36. Bosco A, Anderson S R, Breen K T, Romero C O, Steele M R, Chiodo V A, et al. Complement C3-targeted gene therapy restricts onset and progression of neurodegeneration in chronic mouse glaucoma. *Mol Ther.* 2018; 26:2379-96. doi: 10.1016/j.ymthe.2018.08.017.

37. Nickells R W, Pelzel H R. Tools and resources for analyzing gene expression changes in glaucomatous neurodegeneration. *Exp Eye Res.* 2015; 141:99-110. doi: 10.1016/j.exer.2015.05.009.

38. Smith R S, John S W M, Nishina P M, Sundberg J P. Systematic evaluation of the mouse eye: anatomy, pathology, and biomethods. 1st ed. Boca Raton, FL: CRC Press; 2001.

39. Schlamp C L, Montgomery A D, MacNair C E, Schuart C, Willmer D J, Nickells R W. Evaluation of the percentage of ganglion cells in the ganglion cell layer of the rodent retina. *Mol Vis.* 2013; 19:1387-96.

40. Hendrickson A, Yan Y H, Erickson A, Possin D, Pow D. Expression patterns of calretinin, calbindin and parvalbumin and their colocalization in neurons during development of *Macaca* monkey retina. *Exp Eye Res.* 2007; 85:587-601.

41. Lawrence P M, Studholme K M. Retinofugal projections in the mouse. *J Comp Neurol.* 2014; 522:3733-53. doi: 10.1002/cne.23635.

42. Carrillo G L, Su J, Monavarfeshani A, Fox M A. F-spondin is essential for maintaining circadian rhythms. Front Neural Circuits. 2018. 10.3389/fncir.2018.00013.

43. Benowitz L I, Routtenberg A. GAP-43: an intrinsic determinant of neuronal development and plasticity. *Trends Neurosci.* 1997; 20:84-91. doi: 10.1016/S0166-2236(96)10072-2.

44. Goldner R, Yaron A. TIR axons apart: unpredicted NADase controls axonal degeneration. Neuron. 2017; 93:1239-41.

45. Viar K, Njoku D, Secor McVoy J, Oh U. Sarm1 knockout protects against early but not late axonal degeneration in experimental allergic encephalomyelitis. *PLoS ONE.* 2020; 15:e0235110. doi: 10.1371/journal.pone.0235110.

46. Figley M D, Gu W, Nanson J D, Shi Y, Sasaki Y, Cunnea K, et al. SARM1 is a metabolic sensor activated by an increased NMN/NAD+ ratio to trigger axon degeneration. *Neuron.* 2021; 109:1118-36. doi: 10.1016/j.neuron.2021.02.009.

47. Harun-Or-Rashid M, Pappenhagen N, Zubricky R, Coughlin L, Jassim A H, Inman D M. MCT2 overexpression rescues metabolic vulnerability and protects retinal ganglion cells in two models of glaucoma. *Neurobiol Dis.* 2020; 141:104944. doi: 10.1016/j.nbd.2020.104944.

48. Alavian K N, Li H, Collis L, Bonanni L, Zeng L, Sacchetti S, et al. Bcl-x L regulates metabolic efficiency of neurons through interaction with the mitochondrial F1 FO ATP synthase. *Nat Cell Biol.* 2011; 13:1224-33. doi: 10.1038/ncb2330.

49. Chen Y B, Aon M A, Hsu Y T, Soane L, Teng X, McCaffery J M, et al. Bcl-x L regulates mitochondrial energetics by stabilizing the inner membrane potential. *J Cell Biol.* 2011; 195:263-76. doi: 10.1083/jcb.201108059.

50. Berman S B, Chen Y B, Qi B, McCaffery J M, Rucker E B, Goebbels S, et al. Bcl-x L increases mitochondrial fission, fusion, and biomass in neurons. *J Cell Biol.* 2009; 184:707-19. doi: 10.1083/jcb.200809060.

51. Anderson D R, Hendrickson A. Effect of intraocular pressure on rapid axoplasmic transport in monkey optic nerve. Investig *Ophthalmol Vis Sci.* 1974; 13:771-83.

52. Stieger K, Lheriteau E, Moullier P, Rolling F. AAV-mediated gene therapy for retinal disorders in large animal models. *ILAR J.* 2009; 50:206-24. doi: 10.1093/ilar.50.2.206.

53. Ramirez-Komo J A, Delaney M A, Straign D, Lukin K, Tsang M, Iritani B M, et al. Spontaneous loss of B lineage transcription factors leads to pre-B leukemia in Ebf1+/− Bcl-xLTg mice. *Oncogenesis.* 2017; 6:e355. doi: 10.1038/oncsis.2017.55.

54. Pena J C, Rudin C M, Thompson C B. A Bcl-x(L) transgene promotes malignant conversion of chemically initiated skin papillomas. *Cancer Res.* 1998; 58:2111-6.

55. Wyżewski Z, Świtlik W, Mielcarska M B, Gregorczyk-Zboroch K P. The role of Bcl-xL protein in viral infections. *Int J Mot Sci.* 2021; 22:1-16. doi: 10.3390/ijms22041956.

We claim:

1. A method of treating a subject having a condition associated with apoptosis of a cell, the method comprising administering a therapeutically effective amount of a vector to the subject, wherein the vector comprises a phosphoglycerate kinase (Pgk) promoter operably connected to a polynucleotide encoding an anti-apoptotic BCL2 protein, wherein the Pgk promoter comprises SEQ ID NO: 1, SEQ ID NO: 2, or a sequence having 90% identity to SEQ ID NO:1 or SEQ ID NO:2.

2. The method of claim 1, wherein the anti-apoptotic BCL2 protein is selected from SEQ ID NO:8, SEQ ID NO:10, SEQ ID NO:12, SEQ ID NO:14, SEQ ID NO: 16, SEQ ID NO: 18, SEQ ID NO:20, or sequences 90% identical thereto.

3. The method of claim 2, wherein the anti-apoptotic BCL2 protein comprises SEQ ID NO: 16.

4. The method of claim 3, wherein the Pgk promoter comprises SEQ ID NO: 2.

5. The method of claim 1, wherein the vector is an adenovirus or adenovirus associated viral vector.

6. The method of claim 5, wherein the vector comprises an AAV2 or AAV8 vector.

7. The method of claim 6, wherein the AAV2 vector is an AAV2/2 vector.

8. The method of claim 1, wherein the vector is designed to be self-complementary.

9. The method of claim 1, wherein the condition is selected from the group consisting of glaucoma, multiple sclerosis, hereditary optic neuropathy, traumatic optic nerve injury, ischemic/reperfusion injury of the retina, anterior ischemic optic neuropathy, and other neurodegenerative conditions.

10. The method of claim 9, wherein the condition is glaucoma.

11. The method of claim 10, further comprising administering a therapeutically effective amount of a glaucoma therapeutic.

12. The method of claim 11, wherein the glaucoma therapeutic is selected from the group consisting of a prostaglandin or prostaglandin analog, a beta blocker, an alpha agonist, a carbonic anhydrase inhibitor, a rho kinase inhibitor, and combinations thereof.

13. The method of claim 1, wherein the cells are retinal cells.

14. The method of claim 13, wherein the retinal cells are retinal ganglion cells.

15. The method of claim 1, wherein the vector is administered intraocularly.

16. The method of claim 15, wherein the intraocular administration is via intravitreal injection.

17. The method of claim 1, wherein administration of the vector to an eye of the subject reduces retinal ganglion cell loss after traumatic optic nerve damage in the eye as compared to a control subject not receiving the vector.

18. The method of claim 1, wherein administration of the vector to an eye of a subject with glaucoma reduces retinal ganglion cell degeneration as compared to a control subject not receiving the vector.

19. The method of claim 1, wherein administration of the vector to an eye of a subject with glaucoma reduces the loss of visual function as compared to a control subject not receiving the vector.

20. The method of claim 1, wherein the subject is a human or non-human mammal.

* * * * *